US012714662B2

(12) United States Patent
Arnaud-Roux et al.

(10) Patent No.: US 12,714,662 B2
(45) Date of Patent: Aug. 25, 2026

(54) OILY DISPERSION COMPRISING A POLYMERIC PARTICLE AND A STABILIZER BEARING A $C_9$-$C_{22}$ ALKYL GROUP, AND PROCESS FOR TREATING KERATIN MATERIALS USING THE OILY DISPERSION

(71) Applicant: L'OREAL, Paris (FR)

(72) Inventors: Mireille Arnaud-Roux, Aulnay-sous-Bois (FR); Julien Portal, Aulnay-sous-Bois (FR); Simon Taupin, Aulnay-sous-Bois (FR); Philippe Ilekti, Chevilly Larue (FR)

(73) Assignee: L'OREAL, Paris (FR)

( * ) Notice: Subject to any disclaimer, the term of this patent is extended or adjusted under 35 U.S.C. 154(b) by 1167 days.

(21) Appl. No.: 17/617,614

(22) PCT Filed: Jun. 26, 2020

(86) PCT No.: PCT/EP2020/068143
§ 371 (c)(1),
(2) Date: Dec. 9, 2021

(87) PCT Pub. No.: WO2020/260659
PCT Pub. Date: Dec. 30, 2020

(65) Prior Publication Data

US 2023/0108877 A1 Apr. 6, 2023

(30) Foreign Application Priority Data

Jun. 28, 2019 (FR) ...................................... 1907113

(51) Int. Cl.
*A61K 8/81* (2006.01)
*A61K 8/11* (2006.01)
(Continued)

(52) U.S. Cl.
CPC .............. *A61K 8/8147* (2013.01); *A61K 8/11* (2013.01); *A61Q 1/02* (2013.01); *A61Q 5/00* (2013.01); *A61K 2800/43* (2013.01)

(58) Field of Classification Search
CPC .................................................... A61K 8/8147
See application file for complete search history.

(56) References Cited

U.S. PATENT DOCUMENTS 5,851,517 A * 12/1998 Mougin ............... A61K 8/8152 977/788
10,071,046 B2 * 9/2018 Portal ................... C08F 220/14
(Continued)

FOREIGN PATENT DOCUMENTS

FR 2 937 645 A1 4/2010
FR 3 014 875 A1 6/2015
(Continued)

*Primary Examiner* — Gina C Justice
(74) *Attorney, Agent, or Firm* — POLSINELLI PC

(57) ABSTRACT

The present invention relates to an oily dispersion (A) comprising i) at least one particle consisting of an ethylenic polymer, ii) at least one polymeric stabilizer comprising a ($C_9$-$C_{22}$)alkyl group, and iii) at least one hydrocarbon-based fatty substance which is liquid at 20° C. and 1 atmosphere. The invention also relates to a process for treating keratin materials, notably human keratin materials such as the skin or the hair, involving the application to said materials of at least one oily dispersion (A); to a process for preparing the oily dispersion, and to a multi-compartment kit comprising ingredients i) to iii).

The oily dispersion (A) and the process for treating keratin materials as defined above make it possible to obtain a treatment for said materials which is notably resistant to shampoo washing, to sebum, to sweat and/or to water, but also to fatty substances, notably dietary fatty substances such as oils.

24 Claims, 1 Drawing Sheet

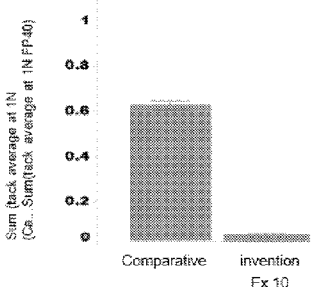

*Tackiness during the drying*

In this protocol, a drop of 10 μL of dispersed polymer in isododecane is deposited on a Byko Chart Lenata contrast card with start of the stopwatch. A series of tack measurements are always carried out at the same place by applying the following protocol: Normal force or load 1N, movement speed 5 mm.s$^{-1}$, contact time: 5 s with a waiting time between each cycle of measurement such that a measurement is made every minute. Results (fig. 2)

(51) Int. Cl.
*A61Q 1/02* (2006.01)
*A61Q 5/00* (2006.01)

(56) References Cited

U.S. PATENT DOCUMENTS

| | | | | |
|---|---|---|---|---|
| 10,745,582 | B2 * | 8/2020 | Farcet | A61Q 3/02 |
| 2002/0164297 | A1 * | 11/2002 | Ferrari | A61K 8/8147 424/70.1 |
| 2016/0317423 | A1 | 11/2016 | Portal et al. | |

FOREIGN PATENT DOCUMENTS

| | | | | |
|---|---|---|---|---|
| FR | 3 029 786 | A1 | | 6/2016 |
| JP | 2007031304 | A | * | 2/2007 |
| JP | 2017501171 | A | | 1/2017 |
| WO | 2015091513 | A1 | | 6/2015 |

* cited by examiner

*Fig. 1*

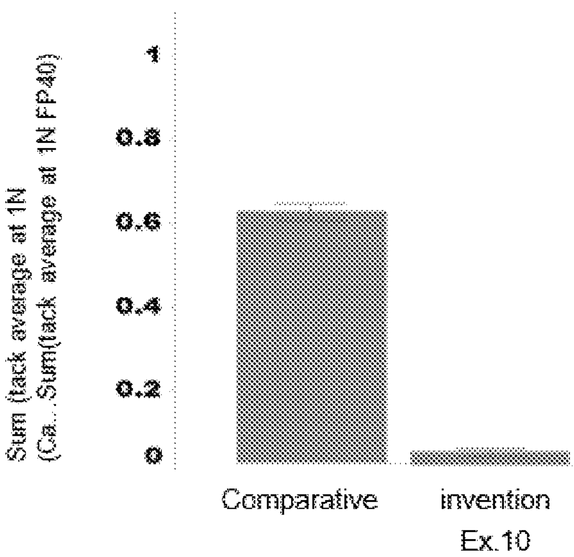

*Tackiness during the drying*

In this protocol, a drop of 10 μL of dispersed polymer in isododecane is deposited on a Byko Chart Lenata contrast card with start of the stopwatch. A series of tack measurements are always carried out at the same place by applying the following protocol: Normal force or load 1N, movement speed 5 $mm.s^{-1}$, contact time: 5 s with a waiting time between each cycle of measurement such that a measurement is made every minute. Results (fig. 2)

*Fig. 2*

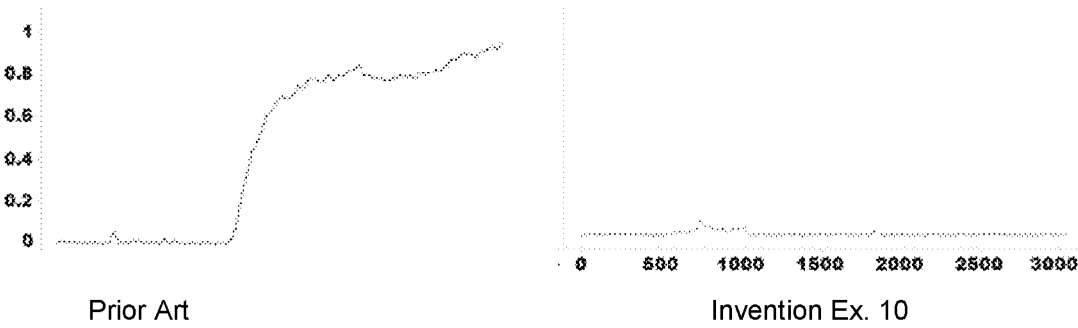

The tackiness during drying is significantly lower for the composition according the invention compared to the prior art composition.

On the other hand none of the tested particle according to the example of the invention smells a strong odour (neither pine nor moldy odours).

OILY DISPERSION COMPRISING A POLYMERIC PARTICLE AND A STABILIZER BEARING A $C_9$-$C_{22}$ ALKYL GROUP, AND PROCESS FOR TREATING KERATIN MATERIALS USING THE OILY DISPERSION

CROSS REFERENCE TO RELATED APPLICATIONS

This application is a National Phase filing under 35 U.S.C. § 371 of PCT/EP2020/068143 filed on 26 Jun. 2020; which application in turn claims priority to Application No. 1907113 filed in France on 28 Jun. 2019. The entire contents of each application are hereby incorporated by reference.

The present invention relates to an oily dispersion (A) comprising i) at least one particle consisting of an ethylenic polymer, ii) at least one polymeric stabilizer comprising a ($C_9$-$C_{22}$)alkyl group, and iii) at least one hydrocarbon-based fatty substance which is liquid at 20° C. and 1 atmosphere. The invention also relates to a process for treating keratin materials, notably human keratin materials such as the skin, the hair or the eyelashes, involving the application to said materials of at least one oily dispersion (A); to a process for preparing the oily dispersion, and to a multi-compartment kit comprising ingredients i) to iii).

During the ageing process, various signs appear on the skin which are very characteristic of this ageing, reflected notably by a change in the skin structure and functions. The main clinical signs of skin ageing are notably the appearance of fine lines and deep wrinkles, which increase with age.

It is known practice to treat these signs of ageing using cosmetic or dermatological compositions containing active agents capable of combating ageing, such as α-hydroxy acids, β-hydroxy acids and retinoids. These active agents act on wrinkles by eliminating dead skin cells and by accelerating the cell renewal process. However, these active agents have the drawback of being effective for the treatment of wrinkles only after a certain application time. Now, it is increasingly sought to obtain an immediate effect of the active agents used, rapidly resulting in smoothing-out of wrinkles and fine lines and in the disappearance of the signs or fatigue.

Cosmetic products often require the use of a film-forming polymer to obtain a deposit of the product on keratin materials that has good cosmetic properties. In particular, it is necessary for the film-forming deposit to have good persistence, in particular for the deposit not to transfer during contact with the fingers or clothing, and also good persistence on contact with water, notably rain or during showering, or else for the deposit to be resistant to perspiration or sebum, and also to dietary fats, notably dietary fatty substances such as oils.

It is known practice to use dispersions of polymer particles, in organic media such as hydrocarbon-based oils. Polymers are notably used as film-forming agents in makeup products such as mascaras, eyeliners, eyeshadows or lipsticks. EP 0 749 747 describes in the examples dispersions in hydrocarbon-based oils (liquid paraffin, isododecane) of acrylic polymers stabilized with polystyrene/copoly(ethylene-propylene) diblock copolymers. The film obtained after application of the dispersion to the skin is sparingly glossy. FR 1 362 795 also describes the use of dispersions of surface-stabilized polymer particles containing hydrocarbon-based oils for making up the lips and eyelashes. WO 2010/046229 describes dispersions in isododecane of acrylic polymers stabilized with stabilizing polymers. FR 1 382 795 describes the use of dispersions of surface-stabilized polymer particles containing hydrocarbon-based oils for making up the lips and the eyelashes.

In the field of dyeing keratin fibres, it is already known practice to dye keratin fibres via various techniques using direct dyes for non-permanent dyeing, or dye precursors for permanent dyeing.

Non-permanent dyeing or direct dyeing consists in dyeing keratin fibres with dye compositions containing direct dyes. These dyes are coloured and colouring molecules that have affinity for keratin fibres. They are applied to the keratin fibres for a time necessary to obtain the desired colouring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, which enables the production of colourings that are visible on dark hair.

It is also known practice to dye keratin fibres permanently via oxidation dyeing. This dyeing technique consists in applying to the keratin fibres a composition containing dye precursors such as oxidation bases and couplers. Under the action of an oxidizing agent, these precursors, form one or more coloured substances in the hair.

The variety of molecules used as oxidation bases and couplers allows a wide range of colours to be obtained, and the colourings resulting therefrom are generally permanent, strong and resistant to external agents, notably to light, bad weather, washing, perspiration and rubbing.

In order to be visible on dark hair, these two dyeing techniques require prior or simultaneous bleaching of the keratin fibres. This bleaching step, performed with an oxidizing agent such as hydrogen peroxide or persalts, results in appreciable degradation of the keratin fibres, which impairs their cosmetic properties. The hair then has a tendency to become coarse, more difficult to disentangle and more brittle.

Another dyeing method consists in using pigments. Specifically, the use of pigment on the surface of keratin fibres generally makes it possible to obtain colourings that are visible on dark hair, since the surface pigment masks the natural colour of the fibre. The use of pigment for dyeing keratin fibres is described, for example, in patent application FR 2 741 530, which recommends using, for the temporary dyeing of keratin fibres, a composition comprising at least one dispersion of film-forming polymer particles including at least one acid function and at least one pigment dispersed in the continuous phase of said dispersion.

The colourings obtained via this dyeing method become removed from the very first shampoo wash.

It is moreover known practice from patent application FR 2 907 678 to perform coloured coatings of the hair using a composition comprising a polysiloxane/polyurea block copolymer and a pigment. However, with such a composition, the coatings obtained may occasionally lack homogeneity and the separation of the hair strands is not always satisfactory.

FR 3 014 875 describes the use of a dispersion of $C_1$-$C_4$ alkyl (meth)acrylate polymer particles surface-stabilized with an isobornyl (meth)acrylate polymeric stabilizer in a non-aqueous medium containing an oil. The deposits obtained using this technology are not always satisfactory, notably in terms or resistance to sebum. On the other hand, the induced odour of the stabilizer such as isobornyl methacrylate is not always satisfactory because it can smell strongly, in particular the odour of pine, or moldy (see for eg: *International Journal of Adhesion and Adhesives,* 78, 182-188 (2017). Those odours must therefore be masked, especially when the stabilizer concentration is high, in order to reach to a more neutral odour.

FR 3 029 788 is focused on makeup dispersions of polymer particles stabilized with at least one stabilizer which is a $C_8$ alkyl (meth)acrylate homopolymer or a copolymer of $C_8$ alkyl (2-ethylhexyl) (meth)acrylate and of $C_1$-$C_4$ alkyl (meth)acrylate. These dispersions are not always satisfactory in terms of resistance to the fatty substances of sebum, which may be a curb on their use in lip makeup, for example. Furthermore, these dispersions may have a feel that is considered too "tacky" after application to the keratin materials, which may be prohibitive for certain applications such as lip or eyelash makeup, etc.

Thus, the aim of the present invention is to provide a composition for treating keratin materials, in particular the skin, preferably human skin and more preferentially facial skin, which is not tacky, has good persistence with respect to external attacking factors, and over time, does not leach, and is resistant to sweat, sebum and oils such as dietary oils. Furthermore, the dispersion may comprise cosmetic active agents such as those for obtaining a skin-tensioning effect, for caring for the body, the face and the hair, for protecting against ultraviolet (UV), or for making up the face, the lips, the eyelashes, the eyebrows and the hair. Said dispersion may notably be intended for care and/or makeup, notably for making up the lips.

Another aim of the present invention is to provide a composition for treating keratin fibres, notably human keratin fibres such as the hair, the eyelashes or the eyebrows, which has good resistance to attacking factors such as brushing, does not leach, is resistant to sweat, sebum, light and bad weather, and is persistent with respect to shampoo washing and to the various attacking factors to which said fibres may be subjected, without degrading said fibres, and while keeping the keratin fibres perfectly individualized. On the other hand the odour of the particles must be as neutral as possible to avoid all problem connected with masking a strong odour because of the presence of said particles in a cosmetic formulation.

The technical problem has been solved by using an oily dispersion (A) for treating keratin materials, notably human keratin materials such as the hair, the eyelashes or the skin, in which the oily dispersion (A) is preferably anhydrous, and comprises:

i) one or more particles including one or more polymers chosen from:
   a) ethylenic homopolymers of ($C_1$-$C_4$)alkyl ($C_1$-$C_4$)(alkyl)acrylate, preferably ($C_1$-$C_4$)alkyl (meth)acrylate;
   b) ethylenic copolymers of b1) ($C_1$-$C_4$)alkyl ($C_1$-$C_4$)(alkyl)acrylate, and of b2) ethylenic monomers comprising one or more carboxyl, anhydride, phosphoric acid, sulfonic acid and/or aryl groups such as benzyl; in particular, b2) is a ($C_1$-$C_4$)(alkyl)acrylic acid, more particularly copolymers of ($C_1$-$C_4$)alkyl (meth)acrylate and of (meth)acrylic acid;
   c) ethylenic homopolymers of ($C_1$-$C_4$)alkyl ($C_1$-$C_4$)(alkyl)acrylate, preferably ($C_1$-$C_4$)alkyl (meth)acrylate; and ii) one or more polymeric stabilizers chosen from:
   d) ethylenic homopolymers of ($C_9$-$C_{22}$)alkyl ($C_1$-$C_6$)(alkyl)acrylate, preferably ($C_9$-$C_{22}$)alkyl (meth)acrylate ethylenic homopolymers; and
   e) ethylenic copolymers of ($C_9$-$C_{22}$)alkyl ($C_1$-$C_6$)(alkyl)acrylate and of ($C_1$-$C_4$)alkyl ($C_1$-$C_4$)(alkyl)acrylate, preferably copolymers of ($C_9$-$C_{22}$)alkyl (meth)acrylate and of ($C_1$-$C_4$)alkyl (meth)acrylate;

iii) one or more hydrocarbon-based liquid fatty substances; and iv) optionally one or more cosmetic active agents chosen from f) dyes, g) pigments; h) active agents for caring for keratin materials, notably the skin, and j) UV (A) and/or (B) screening agents, and m) mixtures thereof.

More particularly, the subject or the invention relates to the use of the oily dispersion (A) as defined previously for treating keratin materials, notably human keratin materials such as the hair, the eyelashes, the eyebrows or the skin, preferably for dyeing keratin fibres and/or for shaping keratin fibres such as the hair, or for making up the skin.

A subject of the invention is also the oily dispersion (A) as defined previously, and also a process for treating keratin materials, notably human keratin materials such as the hair, the eyelashes, the eyebrows or the skin, comprising the application to said fibres of the oily dispersion (A) as defined previously. A subject of the invention is also a kit or device comprising several compartments comprising the ingredients i) to iv) as defined previously.

The oily dispersion (A) and the process for treating keratin materials as defined above make it possible to obtain a treatment for said materials which is notably resistant to shampoo washing, to sebum, to sweat and/or to water, but also to fatty substances, notably dietary fatty substances such as oils. Furthermore, the dispersion is easy to use in compositions, notably cosmetic compositions, is easy to manufacture and remains stable over time. Specifically, the oily dispersion (A) in accordance with the present invention makes it possible to obtain deposits that are very resistant to external attacking factors, notably to sebum and to the fatty substances found in food, in particular liquid fatty substances such as plant oils and in particular olive oil. It appears that the makeup produced with at least one oily dispersion (A), notably lip makeup, is particularly resistant to external attacking factors such as liquid fatty substances, in particular with respect to plant oils such as olive oil. Furthermore, the makeup results obtained with the oily dispersions (A) are very aesthetic and glossy. Furthermore, these dispersions of polymer particles are found at a high solids content in the hydrocarbon-based liquid fatty substance(s) iii). It appears that the application of the oily dispersions (A) of the invention to keratin fibres makes it possible to obtain coatings that are persistent with respect to external attacking factors (sunlight, water, shampoo washing, perspiration, sebum, etc.).

In addition, when the composition comprises one or more dyes and/or pigments, the coloured keratin materials have a colouring that is visible on all types of materials, notably on dark keratin materials, in a persistent manner with respect to soaps, shower gels or shampoos, while at the same time preserving the physical qualities of the keratin material. Such a coating is, in particular, resistant to the external attacking factors to which the keratin fibres, notably the hair, may be subjected, such as blow-drying and perspiration. The use of the oily dispersion (A) on keratin materials, in particular on keratin fibres, makes it possible to obtain a smooth, homogeneous deposit. Moreover, it has been observed, surprisingly, that the keratin fibres remain perfectly individualized, and can be styled without any problem.

For the purposes of the present invention and unless otherwise indicated:

an "alkyl radical" is a linear or branched saturated $C_1$-$C_8$, in particular $C_1$-$C_6$, preferably $C_1$-$C_4$ hydrocarbon-based group such as methyl, ethyl, isopropyl and tert-butyl;

a "($C_9$-$C_{22}$)alkyl" radical is a saturated $C_9$-$C_{22}$, in particular $C_{10}$-$C_{20}$, preferentially $C_{12}$-$C_{18}$ and more preferentially $C_{12}$-$C_{16}$, linear or branched hydrocarbon-based group, such as stearyl, behenyl, isodecyl, lauryl, hexadecyl or myristyl; preferably a "($C_9$-$C_{22}$)alkyl" or $C_9$-$C_{22}$, in particular $C_{10}$-$C_{20}$, preferentially $C_{12}$-$C_{18}$ and more preferentially $C_{12}$-$C_{16}$ groups are linear;

an "alkylene radical" is a linear or branched divalent saturated $C_1$-$C_8$, in particular $C_1$-$C_6$, preferably $C_1$-$C_4$ hydrocarbon-based group such as methylene, ethylene or propylene;

a "cycloalkyl" radical is a saturated cyclic hydrocarbon-based group comprising from 1 to 3 rings, preferably 2 rings, and comprising from 3 to 13 carbon atoms, preferably between 5 and 10 carbon atoms, such as cyclopentyl, cyclohexyl, cycloheptyl, norbornyl, or isobornyl, the cycloalkyl radical possibly being substituted with one or more ($C_1$-$C_4$)alkyl groups such as methyl; preferably, the cycloalkyl group is an isobornyl group.

a "cyclic" radical is a cyclic saturated or unsaturated, aromatic or non-aromatic hydrocarbon-based group comprising from 1 to 3 rings, preferably 1 ring, and comprising from 3 to 10 carbon atoms, such as cyclohexyl or phenyl;

an "aryl" radical is a cyclic unsaturated aromatic radical comprising from 6 to 12 carbon atoms, which is mono- or bicyclic, fused or unfused; preferably, the aryl group comprises 1 ring and to 6 carbon atoms, such as phenyl;

an "aryloxy" radical is an aryl-oxy, i.e. aryl-O—, radical, with aryl as defined previously, preferably phenoxy;

an "aryl($C_1$-$C_4$)alkoxy" radical is an aryl-($C_1$-$C_4$)alkyl-O—, radical, preferably benzoxy;

the term "keratin fibres" particularly means human skin (keratinized epithelium) and human keratin fibres such as head hair, the eyelashes, the eyebrows, and bodily hair, preferentially head hair, the eyebrows and the eyelashes, even more preferentially head hair;

the term "individualized" keratin fibres means keratin fibres, notably the hair, which, after application of the composition and drying, are not stuck together (or of which all the strands are separated from each other) and thus do not form dumps of fibres;

the term "insoluble monomer" thus means any monomer whose homopolymer or copolymer is not in soluble form, i.e. completely dissolved to a concentration of greater than 5% by weight at room temperature (20° C.) in said medium. However, the insoluble monomers may, as monomers, be soluble or insoluble in the hydrocarbon-based liquid fatty substance(s) iii), it being understood that they become insoluble after polymerization in the hydrocarbon-based liquid(s) iii);

the term "ethylenic homopolymer" means a polymer derived from the polymerization of identical monomers;

the term "ethylenic copolymer" means a polymer derived from the polymerization of different monomers, in particular at least two different monomers. Preferably, the ethylenic copolymer of the invention is derived from two or three different monomers, more preferentially derived from two different monomers;

the term "ethylenic monomer" means an organic compound including one or more conjugated or non-conjugated unsaturations of the type >C═C<, which are capable of polymerizing;

the term "soluble monomer" means any monomer whose homopolymer or copolymer, preferably homopolymer, is soluble to at least 5% by weight, at 20° C., in the hydrocarbon-based liquid fatty substance(s) iii) of the dispersion. The homopolymer is completely dissolved in the carbon-based liquid(s) iii), visually at 20° C. i.e. there is no visible sign of any deposit, or precipitate, or agglomerate, or insoluble sediment. However, the soluble monomers may, as monomers, be soluble or insoluble in the carbon-based liquid fatty substance(s) iii), it being understood that they become soluble after polymerization in the hydrocarbon-based liquid(s) iii);

the term "fatty substance" means an organic compound that is insoluble in water at ordinary room temperature (25° C.) and at atmospheric pressure (760 mmHg) (solubility of less than 5%, preferably 1% and even more preferentially 0.1%). They bear in their structure at least one hydrocarbon-based chain including at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane. These fatty substances are neither polyoxyethylenated nor polyglycerolated. They are different from fatty acids, since salified ratty acids constitute soaps that are generally soluble in aqueous media;

the term "liquid" fatty substance notably means a fatty substance that is liquid at 25° C. and 1 atmosphere; preferably, said fatty substance has a viscosity of less than or equal to 7000 centipoises at 20° C.;

the term "hydrocarbon-based" fatty substance means a fatty substance which comprises at least 50% by weight, notably from 50% to 100% by weight, for example from 60% to 99% by weight, or from 65% to 95% by weight, or even from 70% to 90% by weight, relative to the total weight of said fatty substance, of carbon-based compound which is liquid at 25° C., having a global solubility parameter according to the Hansen solubility space of less than or equal to 20 (MPa) ½, or a mixture of such compounds;

the global solubility parameter δ according to the Hansen solubility space is defined in the article "Solubility parameter values" by Grulke in the book "Polymer Handbook", 3rd Edition, Chapter VII, pages 519-559, by the relationship $\delta=(d_D^2+d_P^2+d_H^2)_{1/2}$ in which:—$d_D$ characterizes the London dispersion forces arising from the formation of dipoles induced during molecular impacts,—$d_P$ characterizes the Debye interaction forces between permanent dipoles,—$d_H$ H characterizes the forces of specific interactions (such as hydrogen bonding, acid/base, donor/acceptor, etc.); The definition of solvents in the Hansen three-dimensional solubility space is described in the article by Hansen: *The three-dimensional solubility parameters*, J. Paint Technol. 39, 105 (1967);

the term "oil" means a fatty substance that is liquid at room temperature (25° C.) and at atmospheric pressure;

the term "hydrocarbon-based oil" means an oil formed essentially from, or even constituted of, carbon and hydrogen atoms, and optionally oxygen and nitrogen atoms, and not containing any silicon or fluorine atoms.

It may contain hydroxy, ester, ether, carboxylic acid, amine and/or amide groups;

the term "volatile oil" means an oil (or non-aqueous medium) that can evaporate on contact with keratin materials in less than one hour, at room temperature and at atmospheric pressure. The volatile oil is a volatile cosmetic oil, which is liquid at room temperature, notably having a non-zero vapour pressure, at room temperature and at atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg);

the term "non-volatile oil" means an oil with a vapour pressure of less than 0.13 Pa at room temperature and at atmospheric pressure;

the term "silicone oil" means an oil comprising at least one silicon atom and notably at least one Si—O group. The silicone oil may be volatile or non-volatile;

the term "dispersant" refers to a compound which can protect the dispersed particles from agglomerating or flocculating. This dispersant may be a surfactant, an oligomer, a polymer or a mixture of several thereof, bearing one or more functionalities with strong affinity for the surface of the particles to be dispersed; in particular, they can attach physically or chemically to the surface of the pigments. These dispersants also contain at least one functional group that is compatible with or soluble in the continuous medium. Said agent may be charged: it may be anionic, cationic, zwitterionic or neutral;

the term "pigment" refers to any pigment that gives colour to keratin materials, of synthetic or natural origin, the solubility of the pigments in water at 25° C. and at atmospheric pressure (760 mmHg) being less than 0.05% by weight and preferably less than 0.01%;

the term "lake" refers to dyes adsorbed onto insoluble particles, the assembly thus obtained remaining insoluble during use. The inorganic substrates onto which the dyes are adsorbed are, for example, alumina, silica, calcium sodium borosilicate, calcium aluminium borosilicate and aluminium. Among the organic dyes, mention may be made of cochineal carmine.

The term "hair dyes" refers to the oxidation dyes and direct dyes used for dyeing keratin fibres, notably human keratin fibres such as the hair.

the term "anhydrous" dispersion or composition means a dispersion or composition containing less than 2% by weight of water, or even less than 0.5% of water, and notably free of water; where appropriate, such small amounts of water may notably be provided by ingredients of the composition which may contain residual amounts;

the term "pigments with special effects" refers to pigments that generally create a coloured appearance (characterized by a certain shade, a certain vivacity and a certain level of luminance) that is non-uniform and that changes as a function of the conditions of observation (light, temperature, angles of observation, etc.). They thereby differ from white or coloured pigments that afford a standard uniform opaque, semi-transparent or transparent shade; and the term "submicron" or "submicronic" refers to pigments having a particle size that has been micronized by a micronization method and having a mean particle size of less than a micrometre (μm), in particular between 0.1 and 0.9 μm, and preferably between 0.2 and 0.6 μm.

BRIEF DESCRIPTION OF DRAWINGS

FIG. 1 is a graph of test results of the sebum resistance of the coating obtained from a composition according to the present invention compared to the coating from the composition of FR 3 014 875.

FIG. 2 is a graph of test results of tackiness during drying for the composition according to the present invention compared to the composition of FR 3 014 875.

DETAILED DESCRIPTION OF DISCLOSURE

The oily dispersion (A)

The oily dispersion (A) of the invention comprises i) one or more particles of at least one polymer surface-stabilized with ii) at least one stabilizer in a preferably anhydrous medium, also containing iii) at least one hydrocarbon-based liquid fatty substance.

In order to obtain such a dispersion (A), it is proposed to polymerize particular monomers that are capable of forming the polymeric core i) in the presence of a polymeric statistical stabilizer ii) comprising in major amount a part ii) that is soluble and in minor amount a part i) that is insoluble in the dispersion medium, i.e, in the hydrocarbon-based liquid fatty substance(s).

The dispersions according to the invention thus consist of particles, which are generally spherical, and of at least one surface-stabilized polymer, in an anhydrous medium.

Preferably, said particles i) are not or are sparingly crosslinked.

Polymer Particles i)

The particle(s) of the oily dispersion (A) of the invention preferably consist of one or more polymers chosen from:

a) ethylenic homopolymers of ($C_1$-$C_4$)alkyl ($C_1$-$C_4$)(alkyl)acrylate, preferably ($C_1$-$C_4$)alkyl (meth)acrylate ethylenic homopolymers:

b) ethylenic copolymers of ($C_1$-$C_4$)alkyl ($C_1$-$C_4$)(alkyl) acrylate, preferably ($C_1$-$C_4$)alkyl (meth)acrylate, and or ($C_1$-$C_4$)(alkyl)acrylic acid, preferably (meth)acrylic acid ethylenic copolymers;

c) ethylenic copolymers of ($C_1$-$C_4$)alkyl ($C_1$-$C_4$)(alkyl) acrylate, preferably ($C_1$-$C_4$)alkyl (meth)acrylate ethylenic copolymers; and Preferably, the particle(s) i) consist of an ethylenic polymeric core derived from homopolymers a) or copolymers b) or c) as defined previously.

According to a preferred embodiment of the invention, the polymer constituting the particles i) is an ethylenic acrylate homopolymer a) resulting from the polymerization of an identical monomer of formula (I):

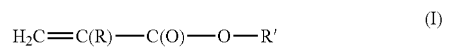

(I)

in which formula (I):

R represents a hydrogen atom or a ($C_1$-$C_4$)alkyl group such as methyl, and

R' represents a ($C_1$-$C_4$)alkyl group such as methyl or ethyl, preferably monomer of formula (I) is a $C_1$-$C_4$ alkyl acrylate such as methyl acrylate.

According to a particular embodiment of the invention, the polymer constituting the particles i) is an ethylenic acrylate copolymer b) resulting from the polymerization:

of at least one monomer of formula (I) as defined previously, preferably a $C_1$-$C_4$ alkyl acrylate such as methyl acrylate and ethyl acrylate; and of a monomer of formula (II)

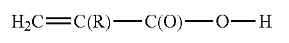

(II)

in which formula (II) R is as defined previously, in particular monomer of formula (II) is acrylic acid.

According to this embodiment, the amount of acrylic acid ranges from 0.1% to 15% by weight relative to the weight of monomers of the particle i) and the polymer of the particles i) is in particular a copolymer derived from the copolymerization of acrylic acid with one or more $C_1$-$C_4$ alkyl (meth)acrylate monomers chosen in particular from methyl (meth)acrylate and ethyl (meth)acrylate.

According to another preferred embodiment of the invention, the polymer constituting the particles i) is an ethylenic acrylate copolymer b) derived from the polymerization:

of at least two different monomers: of formula (I) as defined previously, preferably a $C_1$-$C_4$ alkyl acrylate such as methyl acrylate and ethyl acrylate; and optionally of a monomer of formula (II) as defined previously.

According to a particular embodiment of the invention, the polymer of the particles i) is a polymer derived from $C_1$-$C_4$ alkyl (meth)acrylate monomers. The monomers are preferably chosen from methyl (meth)acrylate, ethyl (meth) acrylate, n-propyl (meth)acrylate, isopropyl (meth)acrylate, n-butyl (meth)acrylate and tert-butyl (meth)acrylate, and more preferentially chosen from methyl (meth)acrylate and ethyl (meth)acrylate.

Advantageously, a $C_1$-$C_4$ alkyl acrylate monomer is used. Preferentially, the monomers are chosen from methyl acrylate and ethyl acrylate.

A $C_1$-$C_4$ alkyl methacrylate monomer is also particularly used. Preferentially, the monomers are chosen from methyl methacrylate and ethyl methacrylate, more particularly methyl methacrylate.

According to a particular embodiment of the invention, the oily dispersion (A) includes from 2% to 40% by weight, in particular 4% to 25%, notably from 5% to 20% by weight of ($C_9$-$C_{22}$)alkyl ($C_1$-$C_6$)(alkyl)acrylate monomers included in d) or e) in the hydrocarbon-based liquid fatty substance(s) iii), relative to the total weight of polymers contained in said dispersion.

According to an advantageous embodiment of the invention, the oily dispersion (A) includes from 60% to 98% by weight, notably from 75% to 96% of monomers a) to c) relative to the total weight of polymers contained in said dispersion.

Preferably, the monomers that are capable of forming the polymeric core of the particle i) are chosen from monomers that are insoluble in the hydrocarbon-based liquid fatty substance(s) iii) of the dispersion (A). The insoluble monomers preferably represent 100% by weight, relative to the total weight of the monomers forming the polymeric core of the particle.

According to one embodiment of the invention, the particles i) include b) ethylenic copolymers of b1) ($C_1$-$C_4$)alkyl ($C_1$-$C_4$)(alkyl)acrylate and of b2) ethylenic monomers comprising one or more carboxyl, anhydride, phosphoric acid, sulfonic acid and/or aryl groups such as benzyl.

More particularly, the ethylenic monomers comprising one or more carboxyl, anhydride, phosphoric acid, sulfonic acid and/or aryl groups are chosen from (1), (2), (3), (4) and (5):

(1) $R^1(R^2)C{=}C(R^3)$-Acid with $R^1$, $R^2$ and $R^3$ representing a hydrogen atom or a $CO_2H$, $H_2PO_4$ or $SO_3H$ group, and Acid representing a carboxyl, phosphoric acid or sulfonic acid, preferably carboxyl, it being understood that $R^1$, $R^2$ and $R^3$ cannot simultaneously represent a hydrogen atom;

(2) $H_2C{=}C(R)$—C(O)—N(R')-Alk-Acid with R and R', which may be identical or different, representing a hydrogen atom or a ($C_1$-$C_4$)alkyl group; Alk represents a ($C_1$-$C_6$)alkylene group optionally substituted with at least one group chosen from Acid as defined previously and hydroxyl; and Acid is as defined previously, preferably carboxyl or sulfonic acid:

(3) Ar—$(R^a)C{=}C(R^b)$—$R^c$ with $R^a$, $R^b$ and $R^c$, which may be identical or different, representing a hydrogen atom or a ($C_1$-$C_4$)alkyl group, and Ar representing an aryl group, preferably benzyl, optionally substituted with at least one acid group $CO_2H$, $H_2PO_4$, or $SO_3H$, preferably substituted with a $CO_2H$ or $SO_3H$ group.

(4) maleic anhydride of formulae (4a) and (4b):

[Chem. 3]

(4a)

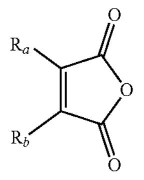

(4b)

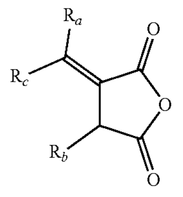

in which formulae (4a) and (4b) $R_a$, $R_b$ and $R_c$, which may be identical or different, represent a hydrogen atom or a ($C_1$-$C_4$)alkyl group; preferably. $R_a$, $R_b$, and $R_c$ represent a hydrogen atom. Preferentially, the ethylenically unsaturated anhydride monomer of the invention is of formula (4b) and more preferentially is maleic anhydride; and (5) $H_2C{=}C(R)$—C(O)—O—H with R representing a hydrogen atom or a ($C_1$-$C_4$)alkyl group such as methyl.

Preferably, b2) is a ($C_1$-$C_4$)(alkyl)acrylic acid, more particularly b) is (are) copolymers of ($C_1$-$C_4$)alkyl (meth) acrylate and of (meth)acrylic acid.

More preferentially, b2) is chosen from crotonic acid, maleic acid, itaconic acid, fumaric acid, styrenesulfonic acid, vinylbenzoic acid, vinylphosphoric acid, acrylic acid, methacrylic acid, acrylamidopropanesulfonic acid, acrylamidoglycolic acid and salts thereof; even more preferentially, b2) represents acrylic acid.

The polymer particles i) of the dispersion (A) preferably have a number-mean size ranging from 5 to 500 nm, notably ranging from 10 to 400 nm and better still ranging from 20 to 300 nm.

The final particle size is preferably greater than 100 nm. In particular, the number-mean size ranges from 100 nm to 500 nm, more particularly ranges from 150 nm to 400 nm and even more particularly ranges from 160 nm to 300 nm.

The mean particle size is determined via standard methods known to those skilled in the art. A Malvern brand NanoZS model laser particle size analyser (which is particularly suitable for submicron dispersions) makes it possible to measure the size distribution of these samples. The operating principle of this type of machine is based on dynamic light scattering (DLS), also known as quasi-elastic light scattering (QELS) or photon correlation spectroscopy (PCS).

The sample is projected into a disposable plastic cuvette (four transparent faces, side length of 1 cm and volume of 4 mL) placed in the measuring cell. The data are analysed on the basis of a cumulative method which leads to a unimodal particle size distribution characterized by an intensity-mean diameter d(nm) and a size polydispersity factor Q. The results may also be expressed in the form of statistical data such as D10; D50 (median), D90 and mode.

Other particle size techniques make it possible to obtain this type of information, such as analysis of the individual tracking of particles (Nanoparticle Tracking Analysis. NTA), laser scattering (LS), acoustic extinction spectroscopy (AES), spatial-filter Doppler velocimetry or image analysis.

The Stabilizer(s) ii)

The dispersion (A) according to the invention also comprises one or more stabilizers ii). Preferably, a single type of stabilizer ii) is used in the invention.

According to a particular embodiment of the invention, the stabilizer(s) ii) are chosen from d) ethylenic homopolymers of ($C_9$-$C_{22}$)alkyl ($C_1$-$C_8$)(alkyl)acrylate, in particular ethylenic homopolymers of ($C_9$-$C_{18}$)alkyl ($C_1$-$C_4$)(alkyl) acrylate, preferably ethylenic homopolymers of ($C_9$-$C_{22}$) alkyl (meth)acrylate and more preferentially ethylenic homopolymers or ($C_9$-$C_{18}$)alkyl (meth)acrylate. Particularly the ($C_9$-$C_{22}$)alkyl or the ($C_9$-$C_{18}$)alkyl groups are linear. According to another variant of the invention the ($C_9$-$C_{22}$) alkyl or the ($C_9$-$C_{18}$)alkyl groups are branched.

More particularly, the stabilizer(s) ii) consist of ethylenic polymers chosen from d) ethylenic homopolymers resulting from the polymerization or monomers of formula $H_2C{=}C(R){-}C(O){-}O{-}R''$ with R representing a hydrogen atom or a ($C_1$-$C_4$)alkyl group such as methyl, and R" representing a ($C_9$-$C_{22}$)alkyl and preferably ($C_9$-$C_{18}$)alkyl group. Preferably, R" represents isodecyl, lauryl, stearyl, hexadecyl or behenyl. According one embodiment of the invention R" represents a linear ($C_9$-$C_{22}$)alkyl and preferably a linear ($C_9$-$C_{18}$)alkyl group.

According to another particular embodiment of the invention, the stabilizer(s) ii) are chosen from e) ethylenic copolymers of ($C_9$-$C_{22}$)alkyl ($C_1$-$C_6$)(alkyl)acrylate and of ($C_1$-$C_4$)alkyl ($C_1$-$C_4$)(alkyl)acrylate, particularly copolymers of ($C_9$-$C_{18}$)alkyl ($C_1$-$C_4$)(alkyl)acrylate and of ($C_1$-$C_4$)alkyl ($C_1$-$C_4$)(alkyl)acrylate, preferably copolymers of ($C_9$-$C_{18}$) alkyl (meth)acrylate and of ($C_1$-$C_4$)alkyl (meth)acrylate.

More preferentially, the stabilizer(s) ii) are chosen from the ethylenic copolymers e) of formulae (III) and (IV):

[Chem 4]

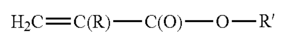

(III)

-continued

[Chem 5]

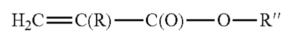

(IV)

in which formulae (III) and (IV);

R, which may be identical or different, represent a hydrogen atom or a ($C_1$-$C_4$)alkyl group such as methyl, R', which may be identical or different, represent a ($C_1$-$C_4$)alkyl group such as methyl or ethyl, and R" represents a ($C_9$-$C_{22}$)alkyl, preferably ($C_{10}$-$C_{20}$) alkyl and in particular ($C_{2n}$)alkyl group with n being an integer equal to 5, 6, 7, 8, 9 or 10. Preferably, R" represents isodecyl, lauryl, stearyl, hexadecyl or behenyl.

Preferentially, the stabilizer(s) ii) are chosen from copolymers derived from monomers chosen from isodecyl, lauryl, stearyl, hexadecyl and behenyl (meth)acrylates and $C_1$-$C_4$ alkyl (meth)acrylate, preferably methyl (meth)acrylate.

More preferentially, the stabilizer(s) ii) are chosen from copolymers derived from monomers chosen from isodecyl, lauryl, stearyl and hexadecyl (meth)acrylates and $C_1$-$C_4$ alkyl (meth)acrylate, preferably methyl (meth)acrylate or ethyl (meth)acrylate.

In particular, the stabilizer ii) is chosen from isodecyl, lauryl, stearyl, hexadecyl or behenyl (meth)acrylate homopolymer and statistical copolymers of isodecyl, lauryl, stearyl, hexadecyl or behenyl (meth)acrylate and of $C_1$-$C_4$ alkyl (meth)acrylate preferably present in a lauryl, stearyl, hexadecyl or behenyl (meth)acrylate/$C_1$-$C_4$ alkyl (meth) acrylate weight ratio of greater than 4.5.

Advantageously, said weight ratio ranges from 5 to 15 and more preferentially said weight ratio ranges from 5.5 to 12.

According to another embodiment, the stabilizer(s) ii) are chosen from ethylenic copolymers e) derived from the polymerization of a monomer of formula (IV) as defined previously and two different monomers of formula (III) as defined previously.

Preferentially, the stabilizer(s) ii) are chosen from copolymers derived from the polymerization of one monomer chosen from isodecyl, lauryl, stearyl, hexadecyl and behenyl (meth)acrylates and of two different $C_1$-$C_4$ alkyl (meth) acrylates, preferably methyl acrylate and ethyl acrylate. In particular, the weight ratio of isodecyl, lauryl, stearyl, hexadecyl or behenyl (meth)acrylates/$C_1$-$C_4$ alkyl (meth)acrylate is greater than 4. Advantageously, said weight ratio ranges from 5 to 15 and more preferentially said weight ratio ranges from 5.5 to 11.

According to another embodiment, the stabilizer(s) ii) are chosen from ethylenic copolymers e) derived from the polymerization of a monomer of formula (III) as defined in the preceding claim and two different monomers of formula (IV) as defined previously.

Preferentially, the stabilizer(s) ii) are chosen from copolymers derived from the polymerization of two different monomers chosen from isodecyl, lauryl, stearyl, hexadecyl and behenyl (meth)acrylates and or one $C_1$-$C_4$ alkyl (meth) acrylate monomer, preferably methyl acrylate and ethyl acrylate; in particular, the weight ratio of isodecyl, lauryl, stearyl, hexadecyl or behenyl (meth)acrylates/$C_1$-$C_4$ alkyl (meth)acrylate is greater than 4.

Advantageously, said weight ratio ranges from 4.5 to 10 and more preferentially said weight ratio ranges from 5 to 8.

According to a particular embodiment of the invention, the oily dispersion (A) includes from 2% to 40% by weight, in particular 4% to 25%, notably from 5.5% to 20% by weight of $(C_9-C_{22})$alkyl $(C_1-C_6)$(alkyl)acrylate monomers included in d) or e) in the hydrocarbon-based liquid fatty substance(s) iii), relative to the total weight of polymers contained in said dispersion.

According to one embodiment of the invention, the stabilizer(s) ii) are chosen from copolymers derived from the polymerization of two different monomers chosen from isodecyl, lauryl, stearyl, hexadecyl and behenyl (meth)acrylates and of one $C_1-C_4$ alkyl (meth)acrylate monomer, preferably methyl acrylate and ethyl acrylate; in particular, the weight ratio of isodecyl, lauryl, stearyl, hexadecyl or behenyl (meth)acrylates/$C_1-C_4$ alkyl (meth)acrylate in the dispersion (A) is less than 1. Particularly, said weight ratio ranges from 0.05 to 0.5 and more preferentially said weight ratio ranges from 0.08 to 0.2 in the dispersion (A).

For these statistical copolymers, the defined weight ratio makes it possible to obtain a polymer dispersion that is stable, notably after storage for seven days at room temperature.

Advantageously, the weight ratio of ii) stabilizer(s) and i) of polymer particle(s) present in the dispersion (A) is between 0.5 and 2, preferably 1.

In particular, the weight ratio of ii) stabilizer(s) and i) polymer particle(s) is less than 1, relative to the total weight of polymers.

According to a particular embodiment of the invention, the stabilizer(s) ii) are present in a content ranging from 2% to 40% by weight, notably from 3% to 30% by weight and preferably from 4% to 25% by weight relative to the weight of polymer(s) present in the dispersion (A).

Preferably, the stabilizer(s) ii) and the particle(s) i) have a number-average molecular weight (Mn) of between 1000 and 1 000 000 g/mol, notably between 5000 and 500 000 g/mol and even better still between 10 000 and 300 000 g/mol.

The dispersion (A) according to the invention is finally formed from polymeric particles of relatively large diameter, i.e. preferably greater than 100 nm, and leads to glossy, film-forming deposits which are resistant to fatty substances at room temperature (25° C.), which are advantageously notably for makeup applications.

The Hydrocarbon-Based Liquid Fatty Substance(s) iii)

The dispersion of polymer particles (A) according to the invention also comprises iii) one or more hydrocarbon-based liquid fatty substances in which said particles are dispersed.

The hydrocarbon-based liquid fatty substances iii) are notably chosen from $C_6-C_{16}$ hydrocarbons or hydrocarbons comprising more than 16 carbon atoms and up to 60 carbon atoms, preferably between $C_6$ and $C_{18}$, and in particular alkanes, oils of animal origin, oils of plant origin, glycerides or fluoro oils of synthetic origin, fatty alcohols, fatty acid and/or fatty alcohol esters, non-silicone waxes, and silicones.

It is recalled that, for the purposes of the invention, the fatty alcohols, fatty esters and fatty acids more particularly contain one or more linear or branched, saturated or unsaturated hydrocarbon-based groups comprising 6 to 60 carbon atoms, which are optionally substituted, in particular with one or more (in particular 1 to 4) hydroxyl groups. If they are unsaturated, these compounds may comprise one to three conjugated or unconjugated carbon-carbon double bonds.

As regards the $C_6-C_{10}$ alkanes, they are linear or branched, and possibly cyclic. Examples that may be mentioned include hexane, dodecane and isoparaffins such as isohexadecane, isodecane and isododecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the hydrocarbon-based liquid fatty substances iii) having a global solubility parameter according to the Hansen solubility space of less than or equal to 20 $(MPa)^{1/2}$, mention may be made of oils, which may be chosen from natural or synthetic, hydrocarbon-based, optionally fluorinated, optionally branched oils, alone or as a mixture.

According to a very advantageous embodiment, the dispersion (A) according to the invention comprises one or more liquid fatty substances which are one or more hydrocarbon-based oils. The hydrocarbon-based oil(s) may be volatile or non-volatile.

According to a preferred embodiment of the invention, the liquid hydrocarbon-based oil(s) are hydrocarbon-based oils which are volatile or are a mixture of different volatile oils, more preferentially chosen from isododecane and octyldodecanol.

According to another particular embodiment, the liquid hydrocarbon-based fatty substance(s) iii) are a mixture of a volatile oil and of a non-volatile oil.

Volatile silicone oils that may be mentioned include volatile linear or cyclic silicone oils, notably those with a viscosity ≤8 centistokes (cSt) ($8\times10^{-6}$ $m^2/s$), and notably containing from 2 to 10 silicon atoms and in particular from 2 to 7 silicon atoms, these silicones optionally including alkyl or alkoxy groups containing from 1 to 10 carbon atoms. As volatile silicone oils that may be used in the invention, mention may notably be made of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes including alkyl, alkoxy and/or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates and pentaphenyl silicone oils.

The hydrocarbon-based oil may be chosen from:

- hydrocarbon-based oils containing from 8 to 14 carbon atoms, and notably:
- branched $C_8-C_{14}$ alkanes, for instance $C_8-C_{14}$ isoalkanes of petroleum origin (also known as isoparaffins), for instance isododecane (also known as 2,2,4,4,6-pentamethylheptane), isodecane and, for example, the oils sold under the trade names Isopar or Permethyl,
- linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in examples 1 and 2 of patent application WO 2008/155059 from the company Cognis, and mixtures thereof,
- short-chain esters (containing from 3 to 8 carbon atoms in total) such as ethyl acetate, methyl acetate, propyl acetate or n-butyl acetate.

hydrocarbon-based oils of plant origin such as triglycerides consisting or fatty acid esters of glycerol, the fatty acids of which may have chain lengths ranging from $C_4$ to $C_{24}$, these chains possibly being linear or branched, and saturated or unsaturated; these oils are notably heptanoic acid or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cotton oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or else caprylic/capric acid triglycerides, for instance those sold by the company Stéarinerie Dubois or those sold under the names Miglyol 810®, 812® and 818® by the company Dynamit Nobel, synthetic ethers containing from 10 to 40 carbon atoms, linear or branched hydrocarbons of mineral or synthetic origin, such as petroleum jelly, polydecenes, hydrogenated polyisobutene such as Parleam®, squalane and liquid paraffins, and mixtures thereof;

esters such as oils of formula $R^1C(O)—O—R^2$ in which $R^1$ represents a linear or branched ratty acid residue including from 1 to 40 carbon atoms and $R^2$ represents an, in particular branched, hydrocarbon-based chain containing from 1 to 40 carbon atoms, on the condition that $R^1+R^2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate:hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

The dispersion (A), in addition to the liquid hydrocarbon-based fatty substance, may comprise a silicone oil. If the silicone oil is in the dispersion (A), it is preferably in an amount which does not exceed 10% by weight relative to the weight of the dispersion (A), more particularly in an amount of less than 5% and preferentially 2%.

In particular, the dispersion (A) comprises at least one liquid hydrocarbon-based fatty substance iii) chosen from:

plant oils formed by fatty acid esters of polyols, in particular triglycerides, such as sunflower oil, sesame oil, rapeseed oil, macadamia oil, soybean oil, sweet almond oil, beauty-leaf oil, palm oil, grapeseed oil, corn oil, arara oil, cottonseed oil, apricot oil, avocado oil, jojoba oil, olive oil or cereal germ oil;

linear, branched or cyclic esters containing more than 6 carbon atoms, notably 6 to 30 carbon atoms; and notably isononyl isononanoate;

and more particularly esters of formula $R^d—C(O)—O—R^e$ in which $R^d$ represents a higher fatty acid residue including from 7 to 19 carbon atoms and $R^e$ represents a hydrocarbon-based chain including from 3 to 20 carbon atoms, such as palmitates, adipates, myristates and benzoates, notably diisopropyl adipate and isopropyl myristate:

hydrocarbons and notably volatile or non-volatile, linear, branched and/or cyclic alkanes, such as $C_5$-$C_{60}$ isoparaffins, which are optionally volatile, such as isododecane, Parleam (hydrogenated polyisobutene), isohexadecane, cyclohexane or isopars; or else liquid paraffins, liquid petroleum jelly, or hydrogenated polyisobutylene;

ethers containing 6 to 30 carbon atoms;

ketones containing 6 to 30 carbon atoms;

aliphatic fatty monoalcohols containing 6 to 30 carbon atoms, the hydrocarbon-based chain not including any substitution groups, such as oleyl alcohol, decanol, dodecanol, octadecanol, octyldodecanol and linoleyl alcohol;

polyols containing 6 to 30 carbon atoms, such as hexylene glycol; and mixtures thereof.

Preferably, the dispersion (A) comprises at least one liquid hydrocarbon-based fatty substance iii) chosen from:

plant oils formed by fatty acid esters of polyols, in particular triglycerides, esters of formula $R^d—C(O)—O—R^e$ in which $R^d$ represents a higher fatty acid residue including from 7 to 19 carbon atoms and $R^e$ represents a hydrocarbon-based chain including from 3 to 20 carbon atoms, volatile or non-volatile, linear or branched $C_6$-$C_{16}$ alkanes.

volatile or non-volatile, non-aromatic cyclic $C_5$-$C_{12}$ alkanes, ethers containing 7 to 30 carbon atoms, ketones containing 8 to 30 carbon atoms, aliphatic fatty monoalcohols containing 12 to 30 carbon atoms, the hydrocarbon-based chain not including any substitution groups, and mixtures thereof.

Advantageously, the liquid hydrocarbon-based fatty substance(s) of the invention are apolar, i.e. formed solely from carbon and hydrogen atoms.

The liquid hydrocarbon-based fatty substance(s) are preferably chosen from hydrocarbon-based oils containing from 8 to 14 carbon atoms, which are in particular volatile, more particularly the apolar oils described previously.

Preferentially, the liquid hydrocarbon-based fatty substance(s) iii) of the invention are isododecane.

According to another advantageous embodiment of the invention, the liquid hydrocarbon-based fatty substance(s) are a mixture of non-volatile oil and volatile oil; preferably, the mixture comprises isododecane as volatile oil. In particular, in the mixture, the non-volatile oil is a phenyl silicone oil, preferably chosen from pentaphenyl silicone oils.

Method for Preparing the Dispersion (A)

Without this being limiting, in general, the dispersion according to the invention may be prepared in the following manner:

The polymerization is performed in dispersion in non-aqueous medium, i.e. by precipitation of the polymer being formed, with protection of the formed particles with one or more stabilizers ii), preferably only one type of stabilizer ii) chosen from d) and e) as defined previously.

In a first step, the stabilizing polymer (or stabilizer ii)) is prepared by mixing the constituent monomer(s) of the stabilizing polymer d) or e) with v) a free-radical initiator, in a solvent known as the synthesis solvent, and by polymerizing these monomers; and then In a second step, the constituent monomer(s) of the polymer of the particles i) are added to the stabilizing polymer formed in the preceding step and polymerization of these added monomers is performed in the presence of the free-radical initiator.

When the non-aqueous medium is a non-volatile liquid hydrocarbon-based fatty substance iii), the polymerization may be performed in an apolar organic solvent (synthesis solvent), followed by adding the non-volatile liquid hydrocarbon-based fatty substance (which should be miscible with said synthesis solvent) and selectively distilling off the synthesis solvent. The cosmetic active agent(s) chosen from f) the dyes and/or pigments; g) the active agents for caring for keratin materials, notably the skin, and h) the UV-screening agents, and also j) mixtures thereof may be added during the first step. According to another variant, the cosmetic active agent(s) are added during the second step or after the second step.

A synthesis solvent which is such that the monomers of the polymeric stabilizer(s) ii) and the free-radical initiator v) are soluble therein, and such that the polymer particles i) obtained are insoluble therein, so that they precipitate therein during their formation, is thus chosen.

In particular, the synthesis solvent chosen is one which is apolar and organic, preferably chosen from alkanes such as heptane, cyclohexane or isododecane, preferably isododecane.

When the non-aqueous medium is a volatile hydrocarbon-based liquid fatty substance iii), the polymerization may be performed directly in said oil, which thus also acts as synthesis solvent. The monomers should also be soluble therein, as should the free-radical initiator, and the polymer of the particles i) which is obtained should be insoluble therein.

The monomers are preferably present in the synthesis solvent, before polymerization, in a proportion of 15% to 45% by weight. The total amount of the monomers may be present in the solvent before the start of the reaction, or part of the monomers may be added gradually as the polymerization reaction proceeds.

The polymerization is preferably performed in the presence v) of one or more radical initiators which may be any initiator known to those skilled in the art for radical polymerization, such as peroxide or azo initiators, redox couples and photochemical initiators.

Mention may notably be made of those of the following types:

peroxide, in particular chosen from tert-butyl peroxy-2-ethylhexanoate: Trigonox 21S: 2,5-dimethyl-2,5-bis(2-ethylhexanoylperoxy)hexane: Trigonox 141: tert-butyl peroxypivalate: Trigonox 25075 from AkzoNobel; or azo, in particular chosen from AIBN: azobisisobutyronitrile; V50: 2,2'-azobis(2-amidinopropane) dihydrochloride.

The polymerization is preferably performed at a temperature ranging from 70 to 110° C. and at atmospheric pressure.

The polymer particles i) are surface-stabilized, when they are formed during the polymerization, by means of the stabilizer ii).

The stabilization may be performed by any known means, and in particular by direct addition of the stabilizer ii), during the polymerization.

The stabilizer ii) is preferably also present in the mixture before polymerization of the monomers of the polymer of the particles i). However, it is also possible to add it continuously, notably when the monomers of the particles i) are also added continuously.

From 4% to 30% by weight and preferably from 4.5% to 20% by weight of the stabilizer(s) may be used relative to the total weight of monomers used (stabilizers ii)+polymer particles i)).

The polymer particle dispersion (A) advantageously comprises from 30% to 65% by weight of solids relative to the total weight of said dispersion and preferably from 40% to 60% by weight relative to the total weight of said dispersion.

The composition according to the invention preferably comprises a solids (or active material) content of polymers of particle i)+dispersing polymers ii) ranging from 10% to 80% by weight, relative to the total weight of composition (A), preferably ranging from 20% to 60% by weight, notably 30% to 50% by weight, relative to the total weight of composition (A).

According to a preferred embodiment of the invention, the dispersion (A) according to the invention is an anhydrous composition.

According to another embodiment of the present invention, the dispersion (A) is in inverse emulsion, i.e. of water-in-oil (W/O) type. In this case, the composition comprises one or more surfactants, which are preferably nonionic. The inverse emulsions of (A) are preferably chosen when the dispersions (A) are intended for makeup, notably for making up the eyelashes and/or the eyebrows.

In one particular preparation method, the statistical stabilizing polymer ii) is prepared in a first step. This stabilizing polymer is soluble in an apolar organic solvent of alkane type, such as isododecane.

Next, in a second step, the polymer particles i) are synthesized in the presence of the stabilizing polymer ii).

Preferentially, a solution of stabilizing polymer ii) in the liquid hydrocarbon-based fatty substance(s) iii) is prepared for the final dispersion, and the polymerization of the monomers which form the core of the particle is performed in the presence of this stabilizer ii).

The stabilizing polymer ii) may be prepared by radical polymerization optionally in the presence of a polymerization initiator v) as defined previously.

In a second step, the monomers which form the core of the particle i) may be polymerized in the presence of said stabilizing polymer ii). This second step may be a conventional radical polymerization.

The dispersions are prepared in the presence of one or more liquid hydrocarbon-based fatty substances iii), preferably in an apolar organic solvent, in particular of alkane type such as isododecane, according to an industrially realistic process.

The dispersions according to the invention are thus finally formed from polymer particles, of relatively large diameter (preferably greater than 100 nm), and give glossy film-forming deposits that are resistant to fatty substances at the observation temperature (25° C.).

Furthermore, since said dispersion is in an oily medium, it becomes easy to formulate it in cosmetic compositions based on an oily medium commonly used in cosmetics, in particular anhydrous media or in the fatty phases of emulsions.

The polymer according to the invention finds a quite particular application in the cosmetic field, notably in the makeup field and notably in lipsticks, glosses (lip glosses) and eyeshadows and mascaras.

The Cosmetic Active Agent(s) iv)

According to a particular embodiment of the invention, the dispersion (A) of the invention comprises one or more cosmetic active agents chosen from f) dyes, g) pigments; h) active agents for caring for keratin materials, and j) UV (A) and/or (B) screening agents, and also k) mixtures thereof.

According to a preferred embodiment of the present invention, the cosmetic active agent(s) of the invention are chosen from f) pigments.

According to a particular embodiment of the present invention, the cosmetic active agent(s) of the invention are chosen from h) active agents for caring for keratin materials, preferably skincare active agents.

According to a particular embodiment of the present patent application, the cosmetic active agent(s) of the invention are chosen from j) UV(A) and/or UV(B) screening agents, and a mixture thereof.

According to a particular embodiment or the invention, dispersion (A) comprises iv) one or more cosmetic active agents chosen from pigments.

The pigment(s) more particularly represent from 0.001% to 10% by weight and preferably from 0.005% to 5% by weight relative to the total weight of the dispersion (A).

The pigments are white or coloured solid particles which are naturally insoluble in the hydrophilic and lipophilic liquid phases usually employed in cosmetics or which are rendered insoluble by formulation in the form of a lake, where appropriate. More particularly, the pigments have little or no solubility in aqueous-alcoholic media.

The pigments that may be used are notably chosen from the organic and/or mineral pigments known in the art, notably those described in Kirk-Othmer's Encyclopedia of Chemical Technology and in Ullmann's Encyclopedia of Industrial Chemistry. Pigments that may notably be mentioned include organic and mineral pigments such as those defined and described in Ullmann's Encyclopedia of Industrial Chemistry "Pigment organics", 2005 Wiley-VCH Verlag GmbH & Co. KGaA, Weinheim 10.1002/14356007.a20 371 and ibid, "Pigments, Inorganic, 1. General" 2009 Wiley-VCH Verlag GmbH & Co. KGaA, Weinheim10.1002/14356007.a20_243.pub3

These pigments may be in pigment powder or paste form. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" refers to any pigment that satisfies the definition in Ullmann's encyclopedia in the chapter on inorganic pigments. Among the mineral pigments that are useful in the present invention, mention may be made of iron oxides, chromium oxides, manganese violet, ultramarine blue, chromium hydrate, ferric blue and titanium oxide.

The pigment may be an organic pigment.

The term "organic pigment" refers to any pigment that satisfies the definition in Ullmann's encyclopedia in the chapter on organic pigments.

The organic pigment may notably be chosen from nitroso, nitro, azo, xanthene, quinoline, anthraquinone, phthalocyanine, metal complex type, isoindolinone, isoindoline, quinacridone, perinone, perylene, diketopyrrolopyrrole, thioindigo, dioxazine, triphenylmethane and quinophthalone compounds.

In particular, the white or coloured organic pigments may be chosen from carmine, carbon black, aniline black, azo yellow, quinacridone, phthalocyanine blue, the blue pigments codified in the Colour Index under the references CI 42090, 69800, 69825, 74100, 74160, the yellow pigments codified in the Colour Index under the references CI 11680, 11710, 19140, 20040, 21100, 21108, 47000, 47005, the green pigments codified in the Colour Index under the references CI 61565, 61570, 74260, the orange pigments codified in the Colour Index under the references CI 11725, 45370, 71105, the red pigments codified in the Colour Index under the references CI 12085, 12120, 12370, 12420, 12490, 14700, 15525, 15580, 15620, 15630, 15800, 15850, 15865, 15880, 26100, 45380, 45410, 58000, 73360, 73915, 75470, the pigments obtained by oxidative polymerization of indole or phenol derivatives as described in patent FR 2 679 771.

Examples that may also be mentioned include pigment pastes of organic pigments, such as the products sold by the company Hoechst under the names:

Cosmenyl Yellow IOG: Yellow 3 pigment (CI 11710);
Cosmenyl Yellow G: Yellow 1 pigment (CI 11680);
Cosmenyl Orange GR: Orange 43 pigment (CI 71105);
Cosmenyl Red R: Red 4 pigment (CI 12085);
Cosmenyl Carmine FB: Red 5 pigment (CI 12490);
Cosmenyl Violet RL: Violet 23 pigment (CI 51319);
Cosmenyl Blue A2R: Blue 15.1 pigment (CI 74160);
Cosmenyl Green GG: Green 7 pigment (CI 74260);
Cosmenyl Black R: Black 7 pigment (CI 77266).

The pigments in accordance with the invention may also be in the form of composite pigments, as described in patent EP 1 184 426. These composite pigments may be composed notably of particles including a mineral core, at least one binder, for attaching the organic pigments to the core, and at least one organic pigment which at least partially covers the core.

The organic pigment may also be a lake. The term "lake" means dyes adsorbed onto insoluble particles, the assembly thus obtained remaining insoluble during use.

The inorganic substrates onto which the dyes are adsorbed are, for example, alumina, silica, calcium sodium borosilicate, calcium aluminium borosilicate and aluminium.

Among the dyes, mention may be made of carminic acid. Mention may also be made of the dyes known under the following names: D&C Red 21 (CI 45 380), D&C Orange (CI 45 370), D&C Red 27 (CI 45 410). D&C Orange 10 (CI 45 425), D&C Red 3 (CI 45 430), D&C Red 4 (CI 15 510). D&C Red 33 (CI 17 200), D&C Yellow 5 (CI 19 140). D&C Yellow 6 (CI 15 985), D&C Green (CI 61 570), D&C Yellow 10 (CI 77 002). D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They thereby differ from coloured pigments that afford a standard uniform opaque, semi-transparent or transparent shade.

Several types or pigments with special effects exist; those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, coloured nacreous pigments such as titanium mica with iron oxides, mica coated with iron oxide, titanium mica notably with ferric blue or with chromium oxide, titanium mica with an organic pigment such as of the abovementioned type, and also nacreous pigments based on bismuth oxychloride. Nacreous pigments that may be mentioned include the Cellini nacres sold by BASF (mica-TiO2-lake), Prestige sold by Eckart (mica-TiO2). Prestige Bronze sold by Eckart (mica-Fe2O3), and Colorona sold by Merck (mica-TiO2-Fe2O3).

Mention may also be made of the gold-coloured nacres sold notably by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold notably by the company Merck under the name Bronze fine (17384) (Colorona) and Bronze (17353) (Colorona) and by the company BASF under the name Super bronze (Cloisonne); the orange nacres sold notably by the company BASF under the name Orange 363C (Cloisonne) and Orange MCR 101 (Cosmica) and by the company Merck under the name Passion orange (Colorona) and Matte orange (17449) (Microna); the brown nacres sold notably by the company BASF under the name Nu-antique copper 340XB (Cloisonne) and Brown CL4509 (Chromalite); the nacres with a copper tint sold notably by the company BASF under the name Copper 340A (Timica); the nacres with a red tint sold notably by the company Merck under the name Sienna fine (17386) (Colorona); the nacres with a yellow tint sold notably by the company BASF under the name Yellow (4502) (Chromalite); the red nacres with a gold tint sold notably by the company BASF under the name Sunstone G012 (Gemtone); the pink nacres sold notably by the company BASF under the name Tan opal. G005 (Gemtone); the black nacres with a gold tint sold notably by the company BASF under the name Nu antique bronze 240 AB (Timica), the blue nacres sold notably by the company Merck under the name Matte blue (17433) (Microna), the white nacres with a silvery tint sold notably by the company Merck under the name Xirona Silver, and the golden-green pink-orange nacres sold notably by the company Merck under the name Indian summer (Xirona), and mixtures thereof.

Still as examples of nacres, mention may also be made of particles including a borosilicate substrate coated with titanium oxide.

Particles comprising a glass substrate coated with titanium oxide are notably sold under the name Metashine MC1080RY by the company Toyal.

Finally, examples of nacres that may also be mentioned include polyethylene terephthalate flakes, notably those sold by the company Meadowbrook Inventions under the name Silver 1P 0.004×0.004 (silver flakes). Multilayer pigments based on synthetic substrates such as alumina, silica, sodium calcium borosilicate or calcium aluminium borosilicate, and aluminium, may also be envisaged.

The pigments with special effects may also be chosen from reflective particles, i.e. notably from particles whose size, structure, notably the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, highlight points that are visible to the naked eye, i.e. more luminous points that contrast with their environment by appearing to sparkle.

The reflective particles may be selected so as not to significantly alter the colouring effect generated by the colouring agents with which they are combined, and more particularly so as to optimize this effect in terms of colour rendition. They may more particularly have a yellow, pink, red, bronze, orange, brown, gold and/or coppery colour or tint.

These particles may have varied forms and may notably be in platelet or globular form, in particular in spherical form.

Irrespective of their form, the reflective particles mayor may not have a multilayer structure, and, in the case of a multilayer structure, may have, for example, at least one layer of uniform thickness, notably of a reflective material.

When the reflective particles do not have a multilayer structure, they may be composed, for example, of metal oxides, notably titanium or iron oxides obtained synthetically.

When the reflective particles have a multilayer structure, they may include, for example, a natural or synthetic substrate, notably a synthetic substrate at least partially coated with at least one layer of a reflective material, notably of at least one metal or metallic material. The substrate may be made of one or more organic and/or mineral materials.

More particularly, it may be chosen from glasses, ceramics, graphite, metal oxides, aluminas, silicas, silicates, notably aluminosilicates and borosilicates, and synthetic mica, and mixtures thereof, this list not being limiting.

The reflective material may include a layer of metal or of a metallic material.

Reflective particles are notably described in JP-A-09188830, JP-A-10158450, JP-A-10158541. JP-A-07258480 and JP-A-05017710.

Still as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the names Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, said substrate being coated with at least one layer of at least one metal oxide, such as titanium oxide, aluminium oxide, iron oxide, cerium oxide, chromium oxide, silicon oxides and mixtures thereof.

Examples that may be mentioned include aluminium powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colours, and also particular optical effects such as metallic effects or interference effects.

The size of the pigment used in the composition according to the present invention is generally between 10 nm and 200 μm, preferably between 20 nm and 80 μm and more preferably between 30 nm and 50 μm.

The pigments may be dispersed in the composition by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters in particular and $C_8$ to $C_{20}$ fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the composition may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described notably in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polyethylene; (meth)acrylic polymers, for example polymethyl methacrylates; polymers and copolymers containing acrylate units; alkanolamines; silicone compounds, for example silicones, in particular polydimethylsiloxanes; organofluorine compounds, for example perfluoroalkyl ethers; fluorosilicone compounds.

The surface-treated pigments that are useful in the composition may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

The organic agent with which the pigments are treated may be deposited on the pigments by solvent evaporation, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is notably described in patent U.S. Pat. No. 4,578,266.

An organic agent covalently bonded to the pigments will preferably be used.

The agent for the surface treatment may represent from 0.1% to 50% by weight of the total weight of the surface-treated pigment, preferably from 0.5% to 30% by weight and even more preferentially from 1% to 20% by weight of the total weight of the surface-treated pigment.

Preferably, the surface treatments of the pigments are chosen from the following treatments:

a PEG-silicone treatment, for instance the AQ surface treatment sold by LCW;—a methicone treatment, for instance the SI surface treatment sold by LCW;

a dimethicone treatment, for instance the Covasil 3.05 surface treatment sold by LCW;

a dimethicone/trimethyl siloxysilicate treatment, for instance the Covasil 4.05 surface treatment sold by LCW;

a magnesium myristate treatment, for instance the MM surface treatment sold by LCW;

an aluminium dimyristate treatment, such as the MI surface treatment sold by Miyoshi;

a perfluoropolymethylisopropyl ether treatment, for instance the FHC surface treatment sold by LCW;

an isostearyl sebacate treatment, for instance the HS surface treatment sold by Miyoshi;

a perfluoroalkyl phosphate treatment, for instance the PF surface treatment sold by Daito;

an acrylate/dimethicone copolymer and perfluoroalkyl phosphate treatment, for instance the FSA surface treatment sold by Daito;

a polymethylhydrosiloxane/perfluoroalkyl phosphate treatment, for instance the FS01 surface treatment sold by Daito;

an acrylate/dimethicone copolymer treatment, for instance the ASC surface treatment sold by Daito;

an isopropyl titanium triisostearate treatment, for instance the ITT surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

According to a particular embodiment of the invention, the dispersant is present with organic or mineral pigments in submicron-sized particulate form in the dye composition.

According to one embodiment, the dispersant and the pigment(s) are present in an amount (dispersant:pigment) of between 1:4 and 4:1, particularly between 1.5:3.5 and 3.5:1 or better still between 1.75:3 and 3:1.

The dispersant(s) may therefore have a silicone backbone, such as silicone polyether and dispersants of aminosilicone type other than the alkoxysilanes described previously. Among the suitable dispersants, mention may be made of:

aminosilicones, i.e. silicones comprising one or more amino groups such as those sold under the names and references: BYK IPX 21879 by BYK. GP-4, GP-6, GP-344, GP-851, GP-965, GP-967 and GP-988-1, sold by Genesee Polymers, silicone acrylates such as Tego® RC 902, Tego® RC 922, Tego® RC 1041, and Tego® RC 1043, sold by Evonik, polydimethylsiloxane (PDMS) silicones with carboxyl groups such as X-22162 and X-22370 by Shin-Etsu, epoxy silicones such as GP-29, GP-32, GP-502, GP-504, GP-514. GP-807. GP-882, and GP-695 by Genesee Polymers, or Tego® 1401, Tego® 1403, Tego® RC 1412 by Evonik.

According to a particular embodiment, the dispersant(s) are of aminosilicone type other than the alkoxysilanes described previously and are cationic.

Preferably, the pigment(s) are chosen from mineral, mixed mineral-organic or organic pigments.

In one variant of the invention, the pigment(s) according to the invention are organic pigments, preferentially organic pigments, surface-treated with an organic agent chosen from silicone compounds. In another variant or the invention, the pigment(s) according to the invention are mineral pigments.

The composition may comprise one or more direct dyes.

The term “direct dye” means natural and/or synthetic dyes, other than oxidation dyes. These are dyes that will spread superficially on the fibre.

They may be ionic or nonionic, preferably cationic or nonionic.

Examples or suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (V) and (VI) and the azo cationic dyes (VI) and (VIII) below:

[Chem. 6]

(V)

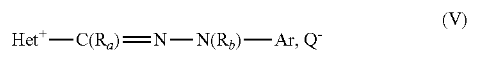

[Chem. 7]

(VI)

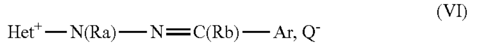

[Chem. 8]

(VII)

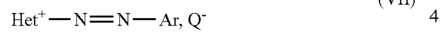

[Chem. 9]

(VIII)

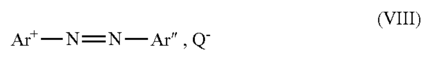

in which formula (V) to (VIII):

- $Het^+$ represents a cationic heteroaryl radical, preferentially bearing an endocyclic cationic charge, such as imidazolium, indolium or pyridinium, which is optionally substituted, preferentially with at least one $(C_1-C_8)$ alkyl group such as methyl;
- $Ar^+$ represents an aryl radical, such as phenyl or naphthyl, bearing an exocyclic cationic charge, preferentially ammonium, particularly tri$(C_1-C_8)$alkylammonium, such as trimethylammonium;
- Ar represents an aryl group, notably phenyl, which is optionally substituted, preferentially with one or more electron-donating groups such as i) optionally substituted $(C_1-C_8)$alkyl, ii) optionally substituted $(C_1-C_8)$alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;
- Ar" represents an optionally substituted (hetero)aryl group, such as phenyl or pyrazolyl, which are optionally substituted, preferentially with one or more $(C_1-C_8)$alkyl, hydroxyl, (di)$(C_1-C_8)$(alkyl)amino, $(C_1-C_8)$alkoxy or phenyl groups;
- Ra and Rb, which may be identical or different, represent a hydrogen atom or a $(C_1-C_8)$alkyl group, which is optionally substituted, preferentially with a hydroxyl group; or else the substituent Ra with a substituent of Het+ and/or Rb with a substituent of Ar form, together with the atoms that bear them, a (hetero)cycloalkyl; in particular, Ra and Rb represent a hydrogen atom or a $(C_1-C_4)$alkyl group optionally substituted with a hydroxyl group;
- Q– represents an organic or mineral anionic counterion, such as a halide or an alkyl sulfate.

In particular, mention may be made of the azo and hydrazono direct dyes bearing an endocyclic cationic charge of formulae (V) to (VIII) as defined previously, more particularly, the cationic direct dyes bearing an endocyclic cationic charge described in patent applications WO 95/15144, WO 95/01772 and EP 714 954, preferentially the following direct dyes:

[Chem. 10]

(IX)

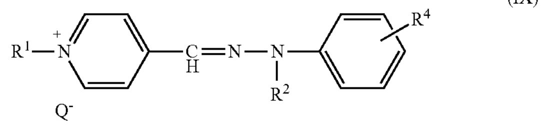

[Chem. 11]

(X)

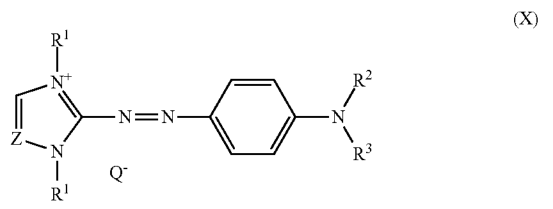

in which formulae (IX) and (X):

- R' represents a $(C_1-C_4)$alkyl group such as methyl;
- $R^2$ and $R^3$, which may be identical or different, represent a hydrogen atom or a $(C_1-C_4)$alkyl group, such as methyl, and
- $R^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) with a hydroxyl group; particularly, $R^4$ is a hydrogen atom,
- Z represents a CH group or a nitrogen atom, preferentially CH,
- Q– is an anionic counterion as defined previously, in particular a halide, such as chloride, or an alkyl sulfate, such as methyl sulfate or mesyl.

In particular, the dyes of formulae (IX) and (X) are chosen from Basic Red 51, Basic Yellow 87 and Basic Orange 31 or derivatives thereof with Q' being an anionic counterion as defined previously, particularly halide such as chloride, or an alkyl sulfate such as methyl sulfate or mesityl.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based poultices or extracts.

According to one embodiment of the invention, the dyes are liposoluble. They are chosen, for example, from Sudan Red, D&C Red 17. D&C Green 6, β-carotene, soybean oil, Sudan Brown, D&C Yellow 11, D&C Violet 2. D&C Orange 5, quinoline yellow and annatto. The water-soluble dyes are, for example, beetroot juice or methylene blue.

Preferably, the cosmetic active agent(s) iv) are chosen from the following pigments: carbon black, iron oxides, notably black, and micas coated with iron oxide, red iron oxides (iron(III) oxide, also known as ferric oxide), triarylmethane pigments, notably blue and violet, such as Blue 1 Lake, azo pigments, notably red, such as D&C Red 7, alkali metal salt of lithol red, such as the calcium salt of lithol red B.

According to a particular embodiment of the invention, the amount of pigments ranges from 0.5% to 40% and preferably from 1% to 20% relative to the weight of the dispersion (A) comprising them.

According to a particular embodiment or the invention, dispersion (A) comprises iv) one or more cosmetic active agents chosen from hair dyes.

Among the hair dyes that may be mentioned are:

- oxidation dyes, which are generally chosen from one or more oxidation bases, optionally combined with one or more coupling agents.

By way of example, the oxidation bases are chosen from para-phenylenediamines, bis(phenyl)alkylenediamines, para-aminophenols, ortho-aminophenols and heterocyclic bases and the corresponding addition salts, optionally combined with coupling agents, in particular chosen from meta-phenylenediamines, meta-aminophenols, meta-diphenols, naphthalene-based coupling agents and heterocyclic coupling agents and also the corresponding addition salts.

- direct dyes, notably azo direct dyes; (poly)methine dyes such as cyanines, hemicyanines and styryls; carbonyl dyes; azine dyes; nitro(hetero)aryl dyes; tri(hetero) arylmethane dyes; porphyrin dyes; phthalocyanine dyes and natural direct dyes, alone or in the form of mixtures. The direct dyes may be anionic, cationic or neutral.
- natural dyes, notably chosen from hennotannic acid, juglone, alizarin, purpurin, carminic acid, kermesic acid, purpurogallin, protocatechaldehyde, indigo, isatin, curcumin, spinulosin, apigenidin and orcein, and also extracts or decoctions containing these natural dyes.

The hair dye(s) more particularly represent from 0.001% to 10% by weight relative to the total weight of the dispersion (A), and preferably from 0.005% to 5% by weight relative to the total weight of the dispersion (A).

Preferably, the pigment(s) of the invention are chosen from carbon black, iron oxides, notably red, brown or black iron oxides, and micas coated with iron oxide, triarylmethane pigments, notably blue and purple triarylmethane pigments, such as Blue 1 Lake, azo pigments, notably red azo pigments, such as D&C Red 7, an alkaline earth metal salt of lithol red, such as the calcium salt of lithol red B; more preferentially, the pigment(s) used are chosen from red iron oxides and azo pigments, notably red azo pigments such as D&C Red 7.

According to a particular embodiment of the invention, the amount of pigments ranges from 0.5% to 40% and preferably from 1% to 20% relative to the weight of the composition and dispersion (A) comprising them.

Process for Treating Keratin Materials Using the Dispersion (A):

According to an advantageous variant of the invention, the process of the invention is a process for treating keratin fibres, in particular human keratin fibres, preferably the hair, which involves the application to said fibres of at least one dispersion (A) as defined previously.

According to a particular embodiment of the invention, after application of the dispersion (A) to the keratin materials, the composition is left to dry on said keratin materials, either naturally or with the aid of heating devices used in cosmetics such as a hairdryer.

According to a particular embodiment of the invention, the process for treating keratin fibres is a process for shaping said fibres.

More particularly, the process for treating keratin fibres involves at least one shaping step, notably:

- in a first step or the process, the keratin fibres are shaped using a conventional shaping means, for example with rollers or a brush of particular shape (cylindrical), and then
- in a second step, the dispersion (A) is applied to said fibres, the application method preferably being by means of a spray, and then
- in a third step, said fibres are dried naturally or dried using conventional devices used in cosmetics, and then
- the shaping means is removed from said fibres, optionally followed by a rinsing step, a step of shampoo washing and then a step of drying naturally or of drying using standard devices.

Once the application of the dispersion (A) has been performed, before the third step, rinsing or shampoo washing may optionally be performed.

The dispersion (A) may be applied to wet or dry, preferably dry, keratin fibres.

It is also possible, via the process for treating keratin fibres of the invention, to perform shaping while at the same time providing said fibres with one or more cosmetic active agents, for example dyeing by applying at least one dye and/or pigment, and/or applying at least one UV(A) and/or UV(B) screening agent, and/or applying at least one care active agent to said fibres. It suffices to apply a dispersion (A) comprising at least one cosmetic agent iv) as defined previously. It also appears that the shaping is persistent and, what is more, that the cosmetic active agent(s) iv) applied are also persistent notably with respect to successive shampoo washing and to light rays.

After the application of the dispersion (A), the fibres may be left to dry or may be dried, for example at a temperature of greater than or equal to 30° C. According to a particular embodiment, this temperature is greater than 40° C. According to a particular embodiment, this temperature is greater than 45° C. and less than 100° C.

Preferably, if the fibres are dried, they are dried, in addition to a supply of heat, with a flow of air obtained using a standard device used in cosmetics such as a hood, a hairdryer, a straightening iron, a Climazon, etc.

During drying, a mechanical action may be exerted on the locks, such as combing, brushing or running the fingers through. This operation may similarly be performed once the fibres have been dried, naturally or otherwise.

When the drying step is performed with a hood or a hairdryer, the drying temperature is between 40 and 110° C. and preferably between 50 and 90° C.

According to one embodiment of the process for treating keratin fibres of the invention, the hair undergoes treatment with a straightening iron. This treatment is then performed once said hair is dry; the temperature of the treatment with the straightening iron is between 110 and 220° C., preferably between 140 and 200° C.

The dispersion (A) described above may be used on wet or dry keratin fibres, and also on any type of fair or dark, natural or dyed, permanent-waved, bleached or relaxed fibres.

According to a particular embodiment of the process of the invention, the fibres are washed before applying the dispersion (A).

The application to the fibres may be performed via any standard means, in particular using a comb, a fine brush, a coarse brush or with the fingers.

According to a preferred embodiment of the invention, the step of applying the dispersion (A) is performed on dry keratin fibres.

According to another particular embodiment of the process of the invention, the step of applying the dispersion (A) is performed on humid or wet keratin fibres.

Preferably, after applying the dispersion (A), there is a waiting time of between 1 minute and 6 hours, in particular between 10 minutes and 5 hours, more particularly between 30 minutes and 4 hours, and preferably about 3 hours, in the open air.

According to another particular embodiment of the invention, the process for treating keratin fibres, notably human keratin fibres such as the hair, is a process for dyeing said fibres comprising at least one step of applying to said fibres a dispersion (A) as defined previously which comprises h) at least one dye, and/or j) at least one pigment, followed by a drying step. Once the application of the dispersion (A) of the invention to the keratin fibres has been performed, rinsing and/or shampoo washing may optionally be performed.

The dispersion (A) may be applied to wet or dry keratin fibres, preferably fibres which have been dried naturally or dried using standard devices used in cosmetics as defined previously.

According to a particular embodiment of the invention, the process for treating keratin materials is a process for treating the skin and/or the eyelashes or the eyebrows involving the application to the skin and/or the eyelashes or the eyebrows of the dispersion (A) as defined previously, followed by a step of drying naturally or of drying using standard devices used in cosmetics as defined previously, preferably naturally.

According to a particular embodiment of the invention, the process for treating keratin materials is a process for making up the skin and/or the eyelashes or the eyebrows, involving a step of applying the dispersion (A) comprising at least one dye and/or at least one pigment, preferably at least one pigment.

The dispersion (A) according to the invention may also comprise a cosmetic additive chosen from fragrances, preserving agents, fillers, waxes, surfactants, moisturizers, vitamins, ceramides, antioxidants, free-radical scavengers, polymers other than a), b), c), d) and e), thickeners, dyestuffs other than f), dyes and g) pigments.

Preferentially, the first step of the process of the invention is the application of the dispersion (A) in one or more apolar solvents, notably isododecane.

The Kit

A subject of the invention is also a kit or device with several separate compartments, comprising:

- in one compartment: the dispersion (A) comprising the ingredients i) to iii) as defined previously, and
- divided among one or more different compartments, the following ingredients: f) dyes, g) pigments; h) active agents for caring for keratin materials, notably the skin, and j) UV (A) and/or (B) screening agents.

The composition packaging assembly is, in a known manner, any packaging that is suitable for storing cosmetic compositions (notably a bottle, tube, spray bottle or aerosol bottle).

The invention is illustrated in greater detail in the examples that follow.

EXAMPLES

The dispersions of polymer particles presented in the various examples were prepared in 1 litre pilot reactors. The syntheses are performed in an apolar aprotic organic solvent such as isododecane.

The synthetic process is identical for all the dispersions obtained. In a first step, the statistical stabilizing polymer is synthesized by reaction between the $C_9$-$C_{22}$ alkyl (meth) acrylate and a small amount or one or two different ($C_1$-$C_4$) alkyl ($C_1$-$C_4$)(alkyl)acrylates, preferably ($C_1$-$C_4$)alkyl (meth)acrylates such as methyl acrylate or methyl acrylate+ ethyl acrylate.

The reaction is performed at 90° C. for 2 hours. In the second step, the particle core is obtained after introducing the ($C_1$-$C_4$)alkyl ($C_1$-$C_4$)(alkyl)acrylate ethylenically unsaturated monomers, preferably ($C_1$-$C_4$)alkyl (meth)acrylate and optionally ($C_1$-$C_4$)(alkyl)acrylic acid, preferably (meth)acrylic acid such as acrylic acid; into the reaction medium containing the stabilizing polymer. This second step is performed at 90° C. for 5 hours.

Several purification steps by distillation of the solvent (isododecane), also known as "strippings", may be performed at the end of the synthesis to remove the residual unreacted monomers.

The percentage of active material in the liquid hydrocarbon-based fatty substance(s) iii) such as isododecane is finally between 40% and 55%. All of the monomers used for the various examples and the polymerization initiator are summarized in Tables 1 and 2 below:

TABLE 1

| Monomers used in the various examples | CAS |
|---|---|
| Hexyl acrylate | 2499-95-8 |
| 2-Ethylhexyl acrylate | 103-11-7 |
| Isodecyl acrylate | 1330-61-6 |
| Lauryl acrylate | 2156-97-0 |
| Stearyl acrylate | 4813-57-4 |
| Behenyl acrylate | 18299-85-9 |
| Isodecyl methacrylate | 29964-85-9 |
| Lauryl methacrylate | 142-90-5 |
| Hexadecyl methacrylate | 2495-27-4 |
| Stearyl methacrylate | 203743-03-7 |
| Methyl acrylate | 96-33-3 |
| Ethyl acrylate | 140-88-5 |
| Acrylic acid | 79-10-7 |

The polymerization initiator is Trigonox T21S. The CAS and the supplier of this initiator are given in Table 2: Polymerization initiator used in the various examples

TABLE 2

| Free-radical initiator | CAS |
|---|---|
| Trigonox 21S | 3006-82-4 |

Various examples of use of the polymers of the invention are presented on various keratin material substrates, notably skin and hair.

Examples of Implementation of the Invention

Synthesis of the Oily Dispersions with a Stabilizer Bearing a $C_9$-$C_{22}$ Alkyl Group An example of synthesis is presented below for producing an oily dispersion with a $C_9$-$C_{22}$ alkyl (meth)acrylate stabilizer. For this example, stearyl methacrylate was used in combination with methyl acrylate for the stabilizing arm and methyl acrylate was adopted for the core of the particle.

Example of Synthesis of a Stearyl Methacrylate/Methyl Acrylate Oily Dispersion Example 13

The oily dispersions are formed as a whole (polymer particles i)+polymeric stabilizer ii)) with 94.5% of methyl acrylate and 5.5% of stearyl methacrylate. The synthesis of these oily dispersions was performed in a 1 litre pilot reactor. The synthesis is performed in two steps:

In a first step, stearyl methacrylate is polymerized in isododecane in the presence of a small amount of methyl acrylate and of a radical initiator (T21S). In the first step, the stearyl methacrylate/methyl acrylate mass ratio is 85/15.

In the second step, the rest of the methyl acrylate is poured in in the presence of isododecane and of the radical initiator (T21S).

After stripping, the polymer is at a solids content of 50% in the isododecane.

The ratios employed to obtain the stabilizer and the core are summarized in Table 3: Specific ratios in the stabilizer and the core for the dispersion

TABLE 3

| | Core composition i) + stabilizer ii) | | | Overall polymer composition | | Stability - |
|---|---|---|---|---|---|---|
| Example | | Monomer | Mass % in g | Monomer | Mass % in g | 1 week at RT* |
| 13 | Stabilizer ii) | Stearyl methacrylate | 85 | Stearyl methacrylate | 5.5 | Fluid |
| | | Methyl acrylate | 15 | | | |
| | | | | Methyl acrylate | 94.5 | |
| | Core i) | Methyl acrylate | 100 | | | |

*RT = room temperature

[Table 4]:

Amounts of reagents used for example 10

Step 1:

| Ingredients | Mass (g) |
|---|---|
| Stearyl methacrylate | 13.75 |
| Methyl acrylate | 2.34 |

-continued

| Ingredients | Mass (g) |
|---|---|
| T21S | 0.16 |
| Isododecane iii) | 60 |

Isododecane Added Between the Two Steps:

| Ingredient | Mass (g) |
|---|---|
| Isododecane iii) | 200 |

Step 2:

| Ingredients | Mass (g) | Mass added to the beaker (g) |
|---|---|---|
| Methyl acrylate | 234 | 269.1 |
| T21S | 2.21 | 2.54 |
| Isododecane iii) | 234 | 269.1 |

Experimental Protocol:

Isododecane, stearyl methacrylate, methyl acrylate and T21S are introduced as feedstock into the reactor. The medium is heated to 90° C. (nominal medium temperature) under argon and with stirring. The solids content during this first step is 22%.

After heating for 2 hours, NMR indicates a stearyl methacrylate consumption of 99% (methyl acrylate consumption: 98%).

After 2 hours of reaction, isododecane is introduced. The medium is heated to 90° C.

Once the medium is at 90° C. methyl acrylate, isododecane and T21S are introduced over 1 hour by pouring. At the end of the introduction, the medium is milky.

After 7 hours of synthesis, virtually total consumption of the methyl acrylate and quantitative consumption of the stearyl methacrylate are obtained.

400 mL of isododecane are then stripped out (the reaction progress is monitored by NMR).

Several syntheses were performed according to this same protocol. Hereinbelow, only the compositions and the nature of the monomers constituting the particles i) (the core) and the polymeric stabilizer ii) are indicated in the various tables below (% m g=mass percentage in g):

TABLE 5

| Ex. | | Core and stabilizer composition Monomer | m % g | Overall polymer composition Monomer | m % g | Stability 1 week at RT |
|---|---|---|---|---|---|---|
| 1 Comp | Stabilizer | Hexyl acrylate | 85 | Hexyl acrylate ($C_6$) | 5.5 | Phase separation with setting to a solid |
| | | Methyl acrylate | 15 | Methyl acrylate | 94.5 | |
| | Core | Methyl acrylate | 100 | | | |
| 2 Comp | Stabilizer | 2-Ethylhexyl acrylate | 85 | 2-Ethylhexyl acrylate ($C_8$) | 5.5 | — |
| | | Methyl acrylate | 15 | Methyl acrylate | 94.5 | |
| | Core | Methyl acrylate | 100 | | | |
| 3 | Stabilizer | Isodecyl acrylate | 85 | Isodecyl acrylate ($C_{10}$) | 5.5 | Fluid |
| | | Methyl acrylate | 15 | Methyl acrylate | 94.5 | |
| | Core | Methyl acrylate | 100 | | | |
| 4 | Stabilizer | Lauryl acrylate | 85 | Lauryl acrylate ($C_{12}$) | 5.5 | Fluid |
| | | Methyl acrylate | 15 | Methyl acrylate | 94.5 | |
| | Core | Methyl acrylate | 100 | | | |

TABLE 6

| Ex. | | Core and stabilizer composition Monomer | m % g | Overall polymer composition Monomer | m % g | Stability 1 week at RT |
|---|---|---|---|---|---|---|
| 5 | Stabilizer | Isodecyl methacrylate | 85 | Isodecyl methacrylate | 5.5 | Fluid |
| | | Methyl acrylate | 15 | Methyl acrylate | 94.5 | |
| | Core | Methyl acrylate | 100 | | | |
| 6 | Stabilizer | Isodecyl methacrylate | 85 | Isodecyl methacrylate | 5.5 | Fluid |
| | | Methyl acrylate | 15 | Methyl acrylate | 94.5 | |
| | Core | Methyl acrylate | 100 | | | |
| 7 | Stabilizer | Isodecyl methacrylate | 85 | Isodecyl methacrylate | 5.5 | Fluid |
| | | Methyl acrylate | 15 | Methyl acrylate | 94.5 | |
| | Core | Methyl acrylate | 100 | | | |
| 8 | Stabilizer | Lauryl methacrylate | 85 | Lauryl methacrylate | 5.5 | Fluid |
| | | Methyl acrylate | 15 | Methyl acrylate | 94.5 | |
| | Core | Methyl acrylate | 100 | | | |
| 9 | Stabilizer | Hexadecyl methacrylate | 85 | Hexadecyl methacrylate | 5.5 | Fluid |
| | | Methyl acrylate | 15 | Methyl acrylate | 94.5 | |
| | Core | Methyl acrylate | 100 | | | |

TABLE 7

| | | | | | | |
|---|---|---|---|---|---|---|
| 10 | Stabilizer | Stearyl methacrylate $C_{16}$ | 85 | Stearyl methacrylate | 5.5 | Fluid |
| | | Methyl acrylate | 15 | Methyl acrylate | 94.5 | |
| | Core | Methyl acrylate | 100 | | | |
| 11 | Stabilizer | Stearyl methacrylate | 89 | Stearyl methacrylate | 10 | Fluid |
| | | Methyl acrylate | 11 | Methyl acrylate | 90 | |
| | Core | Methyl acrylate | 100 | | | |
| 12 | Stabilizer | Stearyl methacrylate | 85 | Stearyl methacrylate | 5.5 | Fluid |
| | | Ethyl acrylate | 7.5 | | | |
| | | Methyl methacrylate | 7.5 | Ethyl acrylate | 74.5 | |
| | Core | Ethyl acrylate | 79 | Methyl methacrylate | 20 | |
| | | Methyl methacrylate | 21 | | | |

TABLE 8

| Ex. | | Core and stabilizer composition Monomer | m % g | Overall polymer composition Monomer | m % g | Stability 1 week at RT |
|---|---|---|---|---|---|---|
| 13 | Stabilizer | Stearyl methacrylate | 85 | Stearyl methacrylate | 5.5 | Fluid |
| | | Methyl acrylate | 10 | | | |
| | | Ethyl acrylate | 5 | Methyl acrylate | 54.5 | |
| | Core | Methyl acrylate | 58 | Ethyl acrylate | 30 | |
| | | Ethyl acrylate | 32 | Acrylic acid | 10 | |
| | | Acrylic acid | 10 | | | |

TABLE 8-continued

| Ex. | | Core and stabilizer composition<br>Monomer | m % g | Overall polymer composition<br>Monomer | m % g | Stability 1 week at RT |
|---|---|---|---|---|---|---|
| 14 | Stabilizer | Stearyl methacrylate | 85 | Stearyl methacrylate | 5.5 | Fluid |
| | | Methyl acrylate | 10 | | | |
| | | Ethyl acrylate | 5 | Methyl acrylate | 70 | |
| | Core | Ethyl acrylate | 58 | Ethyl acrylate | 14.5 | |
| | | Ethyl acrylate | 32 | Acrylic acid | 10 | |
| | | Acrylic acid | 10 | | | |
| 15 | Stabilizer | Stearyl methacrylate | 85 | Stearyl methacrylate | 8 | Fluid |
| | | Methyl acrylate | 7.5 | | | |
| | | Ethyl acrylate | 7.5 | Methyl acrylate | 67 | |
| | Core | Methyl acrylate | 73 | Ethyl acrylate | 15 | |
| | | Ethyl acrylate | 16 | Acrylic acid | 10 | |
| | | Acrylic acid | 11 | | | |

TABLE 9

| Ex. | | Core and stabilizer composition<br>Monomer | m % g | Overall polymer composition<br>Monomer | m % g | Stability 1 week at RT |
|---|---|---|---|---|---|---|
| 16 | Stabilizer | Lauryl methacrylate | 43 | Lauryl methacrylate | 5 | Fluid |
| | | Behenyl acrylate | 43 | Behenyl acrylate | 5 | |
| | | Methyl acrylate | 14 | Methyl acrylate | 90 | |
| | Core | Methyl acrylate | 100 | | | |
| 17 | Stabilizer | Stearyl methacrylate | 43 | Stearyl methacrylate | 5 | Fluid |
| | | Behenyl acrylate | 43 | Behenyl acrylate | 5 | |
| | | Methyl acrylate | 14 | Methyl acrylate | 90 | |
| | Core | Methyl acrylate | 100 | | | |

Evaluations for a Skin Application—Makeup

A formulation containing a particle dispersion of the invention (A) was prepared.

This formulation was applied to an in vitro support such as byko-charts, black scrub panels from the company Byk and left to dry for 24 hours. After 24 hours of drying, evaluations of the deposits are made:

Deposition of 0.5 mL of olive oil or of sebum or of water over 5 minutes onto the deposit.

After 5 minutes of contact, cotton is wiped over 15 times and the degradation of the deposit is observed.

The formulation applied to the in vitro support always has the following composition:

TABLE 10

| Ingredients | Amount in g |
|---|---|
| Polymer of the invention in dispersion (A) | 25% active material |
| Pigment paste: DC Red 7 code 55025 at 40% in isododecane | 6% |
| Isododecane | qs 100 |

TABLE 11

| Example | | Core and stabilizer composition<br>Monomer | m % g | Overall polymer composition<br>Monomer | m % g |
|---|---|---|---|---|---|
| 2 comparative FR 3 029 786 | Stabilizer | 2-Ethyl hexyl acrylate | 85 | 2-Ethylhexyl acrylate | 5.5 |
| | | Methyl acrylate | 15 | Methyl acrylate | 94.5 |
| | Core | Methyl acrylate | 100 | | |
| 3 | Stabilizer | Isodecyl acrylate | 85 | Isodecyl acrylate | 5.5 |
| | | Methyl acrylate | 15 | Methyl acrylate | 94.5 |
| | Core | Methyl acrylate | 100 | | |
| 4 | Stabilizer | Lauryl acrylate | 85 | Lauryl acrylate | 5.5 |
| | | Methyl acrylate | 15 | Methyl acrylate | 94.5 |
| | Core | Methyl acrylate | 100 | | |

Sebum, Olive Oil and Water Resistance Results

TABLE 12

| Ex. | Sebum resistance | Olive oil resistance | Water resistance | Feel |
|---|---|---|---|---|
| 2 (FR 3 029 786) | − | − | + | T |
| 3 | + | + | ++ | NT |
| 4 | + | ++ | ++ | NT |
| 5 | ++ | ++ | ++ | NT |
| 6 | + | ++ | ++ | NT |
| 7 | + | + | ++ | NT |
| 8 | ++ | ++ | ++ | NT |
| 9 | ++ | ++ | ++ | NT |
| 10 | ++ | ++ | ++ | NT |
| 11 | − | + | ++ | NT |
| 12 | ++ | ++ | ++ | NT |
| 13 | + | ++ | ++ | NT |
| 14 | + | + | ++ | NT |
| 15 | − | ++ | ++ | NT |
| 18 | + | ++ | ++ | NT |
| 17 | − | + | ++ | NT |

T: Tacky and
NT: not tacky
(−): no resistance, (+) resistance, (++), very high resistance alter 15 wipes with the same cotton fabric soaked with the same amount at sebum, olive oil or water.

It is seen that the dispersions of the invention make it possible to obtain coatings that are notably persistent with respect to sebum and to the liquid fatty substance such as olive oil, with a pleasant, non-tacky feel, unlike the dispersion of FR 3 029 786 which is not persistent with respect to fatty substances and to sebum and which has unpleasant tackiness after application to the substrate.

Evaluations for a Hair Application—Hair Makeup

Application Protocol:

The various steps of the protocol for applying to keratin fibres (natural hair containing 90% white hairs, also known as 90% NW):

Application to the keratin fibres (dry hair) of composition Ax in a bath ratio of 0.5 g of dispersion or composition/g of hair, The lock is dried with a hairdryer.

The evaluations in terms of resistance to shampoo washing are thus performed 24 hours after the application. The shampoo used is the Ultra Doux shampoo from Garnier.

The various solutions prepared are:

TABLE 13

| Dispersion | A1 | A2 | A3 |
|---|---|---|---|
| Polymer of example 5 | 15% active material | | |
| Polymer of example 8 | | 15% active material | |
| Polymer of example 10 | | | 15% active material |
| Red iron oxide | 6% | 6% | 6% |
| Isododecane | qs 100 | qs 100 | qs 100 |

Results:

Colorimetric Measurements:

The colorimetric data for each of the looks are measured with a Minolta CM-3610d spectrophotometer. In this L* a* b* system, L* represents the lightness, a* indicates the green/red colour axis and b* indicates the blue/yellow colour axis. The higher the value of L, the lighter or less intense the colour. Conversely, the lower the value of L, the darker or more intense the colour. The higher the value of a*, the redder the shade, and the higher the value of b*, the yellower the shade.

The colour build-up on hair thus corresponds to the variation in colouring between the locks of dyed NW hair (natural grey hair containing 90% white hairs) and the non-dyed (i.e. untreated) NW hair, which is measured by (ΔE) according to the following equation:

$$\Delta E=\sqrt{(L^*-L_o^*)^2+(a^*-a_o^*)^2+(b^*-b_o^*)^2} \quad \text{[Math 1]}$$

In this equation, L*, a* and b* represent the values measured after dyeing of the NW hair, and L0*, a0* and b0* represent the values measured before dyeing of the NW hair. The higher the ΔE value, the better the build-up of the colouring.

The results were obtained after dyeing the keratin fibres and then after one shampoo wash for the oily dispersions of the invention.

TABLE 14

| | L | a | b | ΔE |
|---|---|---|---|---|
| Ex. 5 | | | | |
| Before shampooing | 38.86 | 25.39 | 19.77 | 32.67 |
| After shampooing | 39.29 | 26.44 | 20.59 | 33.28 |
| Ex. 10 | | | | |
| Before shampooing | 38.9 | 22.66 | 17.79 | 30.51 |
| After shampooing | 39.7 | 23.07 | 18.38 | 30.29 |

It is seen that the keratin fibres were dyed with pigments with intense and chromatic colours with a good colour build-up ΔE.

Evaluations for a Hair Application—Provision of Body to the Fibre

Application Protocol:

1. A 1 g lock of 90% NW hair 20 cm long is wound around a cylindrical brush to produce curls.
2. 2 g of a dispersion containing the polymer at 10% in isododecane are sprayed onto the lock. The lock was weighed before and after application. About 0.5 g of 10% solution is deposited on the lock.
3. The lock is measured after application and 24 hours after application (lock left at room temperature).
4. A comparison was made with a lock onto which only isododecane was sprayed.

Results:

TABLE 15

| Lock size (cm) | Isododecane | Example 5 | Example 8 | Example 10 |
|---|---|---|---|---|
| $T_0$ | 18 cm | 9 cm | 14 cm | 9 cm |
| T24 h | 18.5 cm | 12 cm | 15 cm | 9 cm |
| Number of curls $T_0$ | 2 | 4 | 4 | 3 |

Conclusion:

The oily dispersions containing the stabilizer bearing a $C_9$-$C_{22}$ alkyl group give body to the hair fibre. The curls obtained after treating the keratin fibres with the dispersions of the invention are very pronounced, with curl heights, i.e. mesh lengths after treatment that are reduced by 30% to 70%), whereas the curls obtained with the liquid hydrocarbon-based fatty substance iii) isododecane are sparingly pronounced, with a very small cud radius and a long coil pitch (to be calculated from the photograph). The examples of the invention all keep a very pronounced curl effect even after 24 hours, unlike the lock treated with the liquid hydrocarbon ratty substance iii) isododecane alone. In particular, Example of stearyl methacrylate/methyl acrylate composition in a 5.5/94.5 mass ratio is very interesting because significant persistence of the cud effect was observed, without any difference in mesh curl length or in the number of curls (3) being observed after 24 hours. This is likewise the case for the lock of Example 8, which, even after 24 hours, does not lose any curls (4).

Additional Data: Comparison of the Oily Dispersions of the Invention Vs. Comparative Oily Dispersion of FR 3 014 875

A comparison was made between a dispersion (A) of the invention and a comparative particle dispersion according to FR 3 014 875.

Example 10 of the invention was compared with the oily dispersion of FR 3 014 875 (Ex. 4) consisting of 20% of isobornyl acrylate, 60% of ethyl acrylate, 10% of methyl acrylate and 10% of acrylic acid.

It is seen that the dispersion of the invention (Example 10) has better resistance to sebum than the comparative composition. This was confirmed by performing a sebum resistance test on a contrast card. Development of substantial tack on FP 40 for the comparative composition is also evidence of the sensitivity to sebum of this starting material by comparison with the dispersion of the invention (Example 10). Specifically, FP 40 contains a plasticizer which mimics sebum. Extraction of this plasticizer by the polymer in the liquid hydrocarbon-based fatty substance iii) isododecane makes it possible to simulate the sensitivity to sebum of the polymer.

TABLE 16

| | Tack on contrast card | Tack on FP40 |
|---|---|---|
| Polymer described in FR 3 014 875 | 0.01 | 0.6 |
| Example 10 | 0.05 | 0.04 |
| | Gloss at 20° on contrast card | Gloss at 20° on FP40 |
| Polymer described in FR 3 014 875 | 69 | 81 |
| Example 10 | 79 | 72 |

Even though the gloss values for the deposits after application of the dispersions according to the invention and the comparative dispersion are similar, the tack during drying is significantly smaller for the dispersion (A) according to the invention (Example 10) relative to the comparative oily dispersion.

Other Sebum, Olive Oil Resistance Results

Drop Test:

Initially, the dispersions of 25% raw material diluted in isododecane are deposited on a contrast card by adjusting the volume deposited/surface in order to obtain a film thickness after drying of the order of 30 μm, which represents, after drying, about 2.7 mg of an active matter/$cm^2$. The deposits are dried 24 hours at 25° C. and 45% Relative Humidity RH to obtain films before being evaluated.

The resistance vs sebum/olive oil is evaluated after having deposited a drop of aggressor (10 μl for sebum or olive oil) on the surface of the deposit. The assessments are made after 1 hour of contact between the Sebum/Oil and the deposit. Results are the followings:

TABLE 17

| Compositions | Sebum resistance | Olive oil resistance |
|---|---|---|
| FR 3 014 875 (comparative) | − | + |
| Ex. 10 (invention) | ++ | ++ |

It is seen that the dispersions of the invention make it possible to obtain coatings that are notably persistent with respect to sebum and to the liquid fatty substance such as olive oil, with a pleasant, non-tacky feel, unlike the dispersion of FR 3 014 875 which is not persistent with respect to fatty substances and to sebum and which has unpleasant tackiness after application to the substrate.

Tackiness Test after One Week of Drying:

The dispersions or 25% raw material diluted in isododecane are deposited on substrates by adjusting the volume deposited/surface in order to obtain a thickness of the film after drying of the order of 30 μm, which represents, after drying, about 2.7 mg of Active material/$cm^2$, Two substrate types are used: a Byko Chart Lenata contrast card without interaction with the formula and an FP40 elastomer—Indeed. FP40 contains a plasticizer mimicking sebum. The extraction of this plasticizer by the polymer in isododecane simulates the sebum sensitivity of the polymer—This elastomer contains a plasticizer which is extracted by solvents such as isododecane and which, under such conditions, interacts with the deposit formed. In the past, we have observed that this plasticizer interacts in the same way as sebum with most of the deposits formed and we use it to mimic the appearance of sebum. The film obtained from composition according to invention (Ex. 10) has better sebum resistance compared to the coating obtained from composition according to the prior art FR 3 014 875 (FIG. 1). A significant development of tights on FP40 of the FR 3 014 875 testifies to the sebum sensitivity of this raw material compared to the one according to the invention.

Tackiness During the Drying

In this protocol, a drop of 10 μL of dispersed polymer in isododecane is deposited on a Byko Chart Lenata contrast card with start of the stopwatch. A series of tack measurements are always carried out at the same place by applying the following protocol: Normal force or load 1N, movement speed 5 $mm \cdot s^{-1}$, contact time: 5 s with a waiting time between each cycle of measurement such that a measurement is made every minute. Results (FIG. 2) The tackiness during drying is significantly lower for the composition according the invention compared to the composition of FR 3 014 875.

On the other hand none of the tested particle according to the example of the invention smells a strong odour (neither pine nor moldy odours).

The invention claimed is:

1. An oily dispersion comprising:

i) one or more particles including one or more polymers chosen from:

a) ethylenic homopolymers of ($C_1$-$C_4$)alkyl ($C_1$-$C_4$)(alkyl)acrylate;

b) ethylenic copolymers of b1) ($C_1$-$C_4$)alkyl ($C_1$-$C_4$)(alkyl)acrylate, and of b2) ethylenic monomers comprising one or more carboxyl, anhydride, phosphoric acid, sulfonic acid and/or aryl groups; and ii) one or more polymeric stabilizers chosen from:

d) ethylenic homopolymers of ($C_9$-$C_{22}$)alkyl ($C_1$-$C_6$)(alkyl)acrylate; and e) ethylenic copolymers of ($C_9$-$C_{22}$)alkyl ($C_1$-$C_6$)(alkyl)acrylate and of ($C_1$-$C_4$)alkyl ($C_1$-$C_4$)(alkyl)acrylate, wherein the ethylenic copolymers have a weight ratio of the $(C_9\text{-}C_{22})$alkyl $(C_1\text{-}C_6)$(alkyl)acrylate/$(C_1\text{-}C_4)$alkyl $(C_1\text{-}C_4)$(alkyl)acrylate of greater than 4;

iii) one or more hydrocarbon-based liquid fatty substances; and iv) optionally one or more cosmetic active agents chosen from f) dyes, g) pigments; h) active agents for caring for keratin materials, and j) UV (A) and/or (B) screening agents, and m) mixtures thereof.

2. The oily dispersion according to claim 1, in which the particles i) consist of an ethylenic polymeric core obtained from homopolymers a) or from copolymers b) and ii) of one or more polymeric surface stabilizers obtained from homopolymer d) and the copolymers e).

3. The oily dispersion according to claim 1, in which the polymer(s) constituting the particles i) are chosen from acrylate ethylenic homopolymers c) resulting from the polymerization of an identical monomer of formula (I):

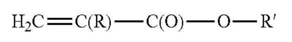

(I)

in which formula (I):

R represents a hydrogen atom or a $(C_1\text{-}C_4)$alkyl group, and

R' represents a $(C_1\text{-}C_4)$alkyl group.

4. The oily dispersion according to claim 1, in which the polymer(s) constituting the particles i) are chosen from acrylate ethylenic copolymers b) resulting from the polymerization:

of at least two different monomers of formula (I):

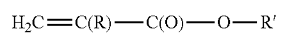

(I)

in which formula (I):

R represents a hydrogen atom or a $(C_1\text{-}C_4)$alkyl group, and

R' represents a $(C_1\text{-}C_4)$alkyl group;

and optionally of a monomer of formula (II) $H_2C{=}C(R)—C(O)—O—H$ wherein R represents a hydrogen atom or a $(C_1\text{-}C_4)$alkyl group.

5. The oily dispersion according to claim 1, in which the monomers are chosen from $C_1\text{-}C_4$ alkyl (meth)acrylates.

6. The oily dispersion according to claim 1, in which the oily dispersion includes from 60% to 98% by weight of monomers a) or b) relative to the total weight of the one or more polymers and the one or more polymeric stabilizers contained in said dispersion.

7. The oily dispersion according to claim 1, in which the stabilizer(s) ii) are chosen from d) ethylenic homopolymers of $(C_9\text{-}C_{22})$alkyl $(C_1\text{-}C_6)$(alkyl)acrylate.

8. The oily dispersion according to claim 1, in which the stabilizer(s) ii) are chosen from isodecyl, lauryl, stearyl, hexadecyl or behenyl (meth)acrylate homopolymer and statistical copolymers of isodecyl, lauryl, stearyl, hexadecyl or behenyl (meth)acrylate and of $C_1\text{-}C_4$ alkyl (meth)acrylate.

9. The oily dispersion according to claim 1, in which the stabilizer(s) ii) are chosen from e) ethylenic copolymers of $(C_9\text{-}C_{22})$alkyl $(C_1\text{-}C_6)$(alkyl)acrylate and of $(C_1\text{-}C_4)$alkyl $(C_1\text{-}C_4)$(alkyl)acrylate.

10. The oily dispersion according to claim 1, in which the stabilizers(s) ii) are chosen from ethylenic copolymers e) resulting from the polymerization of a monomer of formula (IV) and of two different monomers of formula (III)

(III)

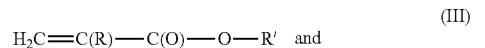

and (IV)

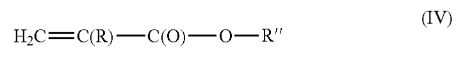

in which formulae (III) and (IV):

R, which may be identical or different, represent a hydrogen atom or a $(C_1\text{-}C_4)$alkyl group, R', which may be identical or different, represent a $(C_1\text{-}C_4)$alkyl group and R" represents a $(C_9\text{-}C_{22})$alkyl.

11. The oily dispersion according to claim 10, in which the stabilizers(s) ii) are chosen from statistical copolymers resulting from the polymerization of two different monomers chosen from isodecyl, lauryl, stearyl, hexadecyl or behenyl (meth)acrylates and of one $C_1\text{-}C_4$ alkyl (meth) acrylate monomer.

12. The oily dispersion according to claim 1, in which the oily dispersion includes from 2% to 40% by weight of $(C_9\text{-}C_{22})$alkyl $(C_1\text{-}C_6)$(alkyl)acrylate monomers included in d) or e) with the hydrocarbon-based liquid(s) iii), relative to the total weight of the one or more polymers and the one or more polymeric stabilizers contained in said dispersion.

13. The oily dispersion according to claim 1, in which the weight ratio of ii) the stabilizer(s) and i) of the polymer particle(s) present in the dispersion (A) is between 0.5 and 2.

14. The oily dispersion according to claim 1, in which the ii) stabilizer(s)+ii) polymer particle(s) assembly present in the dispersion (A) comprises from 2% to 40% by weight relative to the total weight of the dispersion.

15. The oily dispersion according to claim 1, in which the liquid hydrocarbon-based fatty substance(s) iii) are chosen from hydrocarbons, oils of animal origin, oils of plant origin, glycerides or fluorinated oils of synthetic origin, fatty alcohols, esters of fatty acids and/or of fatty alcohols, non-silicone waxes, and silicones.

16. The oily dispersion according to claim 1, in which the liquid hydrocarbon-based fatty substance(s) iii) are chosen from:

plant oils formed by fatty acid esters of polyols;

linear, branched or cyclic esters containing more than 6 carbon atoms;

ethers containing 6 to 30 carbon atoms;

ketones containing 6 to 30 carbon atoms;

aliphatic fatty monoalcohols containing 6 to 30 carbon atoms, the hydrocarbon-based chain not including any substitution groups;

polyols containing 6 to 30 carbon atoms; and mixtures thereof.

17. The oily dispersion according to claim 1, in which the liquid hydrocarbon-based fatty substance(s) iii) are present in the dispersion in a content ranging from 60% to 100% by weight relative to the total weight of the liquid hydrocarbon-based fatty substances present in the dispersion and from 0 to 40% by weight of silicone oil.

18. The oily dispersion according to claim 1, in which the cosmetic active agent(s) iv) are chosen from f) dyes.

19. The oily dispersion according to claim 1, in which the cosmetic active agent(s) iv) are chosen from:

organic pigments and mineral or inorganic pigments.

20. The oily dispersion according to claim 1, which comprises from 60% to 98% by weight of monomers a) or b) relative to the total weight of the one or more polymers and the one or more polymeric stabilizers contained in said dispersion; and from 2% to 40% by weight of the ($C_9$-$C_{22}$) alkyl ($C_1$-$C_6$)(alkyl)acrylate monomers included in d) or e) with the hydrocarbon-based liquid(s) iii), relative to the total weight of the one or more polymers and the one or more polymeric stabilizers contained in said dispersion; and wherein the e) ethylenic copolymers have a weight ratio of the ($C_9$-$C_{22}$)alkyl ($C_1$-$C_6$)(alkyl)acrylate/($C_1$-$C_4$)alkyl ($C_1$-$C_4$)(alkyl)acrylate of 5 to 15.

21. A process for treating keratin materials comprising applying to said materials of the oily dispersion as defined in claim 1 and after application of the dispersion to the keratin materials, the composition being left to dry on said keratin materials either naturally or with the aid of heating devices used in cosmetics.

22. A process for preparing the oily dispersion as defined in claim 1, comprising the following steps:

in a first step, the stabilizer ii) is prepared by mixing the constituent monomer(s) of the stabilizing polymer d) or e) with v) a free-radical initiator, in a solvent, and by polymerizing these monomers; and in a second step, the constituent monomers of the polymer of the particles i) are added to the stabilizer formed in the preceding step and polymerization of these added monomers is performed in the presence of the free-radical initiator;

it being understood that:

when the non-aqueous medium is a non-volatile liquid hydrocarbon-based fatty substance iii), the polymerization may be performed in an apolar organic solvent and the non-volatile liquid hydrocarbon-based fatty substance is then added and the synthesis solvent may be selectively distilled off;

when the non-aqueous medium is a volatile liquid hydrocarbon-based fatty substance iii), the polymerization may be performed directly in said oil, which also acts as synthesis solvent;

the chosen cosmetic active agent(s) iv) may be added during the first step or the cosmetic active agent(s) are added during the second step or after the second step; and the monomers of the stabilizing polymer ii), and the radical initiator v), are soluble in the synthesis solvent, and the polymer particles obtained are insoluble therein.

23. A process for treating keratin materials which comprises applying the oily dispersion as defined in claim 1 to the keratin materials.

24. A kit or device with several separate compartments comprising the oily dispersion as defined in claim 1, and wherein the kit or device comprises:

in one compartment: the ingredients i) to iii), and divided among one or more different compartments, the following ingredients: f) dyes, g) pigments; h) active agents for caring for keratin materials and j) UV (A) and/or (B) screening agents.

* * * * *